United States Patent
Nicholas et al.

(10) Patent No.: US 7,322,994 B2
(45) Date of Patent: Jan. 29, 2008

(54) ANASTOMOSIS INSTRUMENT AND METHOD

(75) Inventors: David A. Nicholas, Trumbull, CT (US); Robert C. Smith, Hamden, CT (US); Scott E. Manzo, Shelton, CT (US)

(73) Assignee: United States Surgical Corporation, North Haven, CT (US)

( * ) Notice: Subject to any disclaimer, the term of this patent is extended or adjusted under 35 U.S.C. 154(b) by 698 days.

(21) Appl. No.: 10/642,918

(22) Filed: Aug. 18, 2003

(65) Prior Publication Data

US 2004/0078047 A1 Apr. 22, 2004

Related U.S. Application Data

(63) Continuation of application No. 10/191,599, filed on Jul. 8, 2002, now Pat. No. 6,726,697, which is a continuation of application No. 09/875,411, filed on Jun. 6, 2001, now Pat. No. 6,440,146, and a continuation of application No. 09/584,541, filed on Jun. 1, 2000, now Pat. No. 6,391,039, which is a continuation of application No. 09/256,260, filed on Feb. 23, 1999, now Pat. No. 6,083,234, which is a continuation-in-part of application No. 08/877,701, filed on Jun. 17, 1997, now Pat. No. 6,024,748, which is a continuation-in-part of application No. 08/685,385, filed on Jul. 23, 1996, now Pat. No. 5,707,380.

(60) Provisional application No. 60/102,326, filed on Sep. 28, 1998.

(51) Int. Cl.
*A61B 17/08* (2006.01)

(52) U.S. Cl. .................. 606/153; 227/175.1; 606/142
(58) Field of Classification Search .. 606/175.1–182.1, 606/142, 143, 151, 153, 154; 227/175.1–182.1
See application file for complete search history.

(56) References Cited

U.S. PATENT DOCUMENTS

| 2,968,041 A | 1/1961 | Skold |
| 3,152,336 A | 10/1964 | Brady |
| 3,232,089 A | 2/1966 | Samuels et al. |

(Continued)

FOREIGN PATENT DOCUMENTS

EP 384647 A1 2/1990

(Continued)

OTHER PUBLICATIONS

PCT/US03/18295, International Search Report dated Oct. 28, 2003.

(Continued)

*Primary Examiner*—Michael J. Hayes
*Assistant Examiner*—Michael Mendoza

(57) ABSTRACT

A surgical instrument for performing an anastomosis includes a housing having proximal and distal ends and a shaft extending from the distal end of the housing. The instrument also includes an actuator attached to the housing and a disposable loading unit configured for selective attachment to the shaft. The disposable loading unit includes a fastener support member configured and dimensioned to support an array of surgical fasteners thereon and a fastener pusher member which is movable through a firing stroke in response to movement of the actuator to deform the surgical fasteners.

4 Claims, 24 Drawing Sheets

U.S. PATENT DOCUMENTS

| | | |
|---|---|---|
| 3,366,301 A | 1/1968 | Mallina |
| 3,519,187 A | 7/1970 | Kapitanov et al. |
| 3,575,038 A | 4/1971 | Mallett |
| 3,741,025 A | 6/1973 | Russell |
| 3,856,016 A | 12/1974 | Davis |
| 3,908,662 A | 9/1975 | Razlov et al. |
| 3,954,108 A | 5/1976 | Davis |
| 4,152,920 A | 5/1979 | Green |
| 4,166,466 A | 9/1979 | Jarvik |
| 4,201,314 A | 5/1980 | Samuels et al. |
| 4,226,242 A | 10/1980 | Jarvik |
| 4,242,902 A | 1/1981 | Jarvik |
| 4,299,224 A | 11/1981 | Noiles |
| 4,316,468 A | 2/1982 | Klieman et al. |
| 4,325,376 A | 4/1982 | Klieman et al. |
| 4,350,160 A | 9/1982 | Kolesov et al. |
| 4,368,736 A | 1/1983 | Kaster |
| 4,372,316 A | 2/1983 | Blake, III et al. |
| 4,408,603 A | 10/1983 | Blake, III et al. |
| 4,412,539 A | 11/1983 | Jarvik |
| 4,425,915 A | 1/1984 | Ivanov |
| 4,430,997 A | 2/1984 | DiGiovanni et al. |
| 4,452,376 A | 6/1984 | Klieman et al. |
| 4,466,436 A | 8/1984 | Lee |
| 4,480,640 A | 11/1984 | Becht |
| D276,650 S | 12/1984 | Green et al. |
| 4,488,543 A | 12/1984 | Tornier |
| 4,493,317 A | 1/1985 | Klaue |
| 4,503,848 A | 3/1985 | Caspar et al. |
| 4,509,518 A | 4/1985 | McGarry et al. |
| 4,522,207 A | 6/1985 | Klieman et al. |
| 4,532,925 A | 8/1985 | Blake, III |
| 4,534,351 A | 8/1985 | Rothfuss et al. |
| 4,586,503 A | 5/1986 | Kirsch et al. |
| 4,598,711 A | 7/1986 | Deniega |
| 4,611,595 A | 9/1986 | Klieman et al. |
| 4,616,650 A | 10/1986 | Green et al. |
| 4,700,703 A | 10/1987 | Resnick et al. |
| 4,712,549 A | 12/1987 | Peters et al. |
| 4,733,664 A | 3/1988 | Kirsch et al. |
| 4,759,364 A | 7/1988 | Boebel |
| 4,809,695 A | 3/1989 | Gwathmey et al. |
| 4,821,939 A | 4/1989 | Green |
| 4,872,874 A | 10/1989 | Taheri |
| 4,883,176 A | 11/1989 | Hart et al. |
| 4,929,240 A | 5/1990 | Kirsch et al. |
| 4,930,674 A | 6/1990 | Barak |
| 4,979,954 A | 12/1990 | Gwathmey et al. |
| 4,983,176 A | 1/1991 | Cushman et al. |
| 5,025,779 A | 6/1991 | Bugge |
| 5,030,226 A | 7/1991 | Green et al. |
| 5,057,111 A | 10/1991 | Park |
| 5,104,395 A | 4/1992 | Thornton et al. |
| 5,108,395 A | 4/1992 | Laurain |
| 5,112,343 A | 5/1992 | Thornton |
| 5,122,150 A | 6/1992 | Puig et al. |
| 5,127,912 A | 7/1992 | Ray et al. |
| 5,147,361 A | 9/1992 | Ojima et al. |
| 5,188,638 A | 2/1993 | Tzakis |
| 5,192,288 A | 3/1993 | Thompson et al. |
| 5,211,649 A | 5/1993 | Kohler et al. |
| 5,222,963 A | 6/1993 | Brinkerhoff et al. |
| 5,234,447 A | 8/1993 | Kaster et al. |
| 5,282,810 A | 2/1994 | Allen et al. |
| 5,314,436 A | 5/1994 | Wilk |
| 5,324,290 A | 6/1994 | Zdeblick et al. |
| 5,340,360 A | 8/1994 | Stefanchik |
| 5,346,115 A | 9/1994 | Perouse et al. |
| 5,346,501 A | 9/1994 | Regula et al. |
| 5,354,304 A | 10/1994 | Allen et al. |
| 5,364,399 A | 11/1994 | Lowery et al. |
| 5,366,462 A | 11/1994 | Kaster et al. |
| 5,403,333 A | 4/1995 | Kaster et al. |
| 5,403,338 A | 4/1995 | Milo |
| 5,423,826 A | 6/1995 | Coates et al. |
| 5,425,738 A | 6/1995 | Gustafson et al. |
| 5,431,668 A | 7/1995 | Burbank, III et al. |
| 5,437,684 A | 8/1995 | Calabrese et al. |
| 5,443,198 A | 8/1995 | Viola et al. |
| 5,452,733 A | 9/1995 | Sterman et al. |
| 5,454,824 A | 10/1995 | Fontayne et al. |
| 5,485,947 A * | 1/1996 | Olson et al. ............ 227/176.1 |
| 5,486,187 A | 1/1996 | Schenck |
| 5,501,698 A | 3/1996 | Roth et al. |
| 5,503,617 A | 4/1996 | Jako |
| 5,549,612 A | 8/1996 | Yapp et al. |
| 5,669,918 A | 9/1997 | Balazs et al. |
| 5,695,504 A | 12/1997 | Gifford, III et al. |
| 5,702,412 A | 12/1997 | Popov et al. |
| 5,707,380 A | 1/1998 | Hinchliffe et al. |
| 5,709,335 A | 1/1998 | Heck |
| 5,725,537 A | 3/1998 | Green et al. |
| 5,732,872 A | 3/1998 | Bolduc et al. |
| 5,762,256 A | 6/1998 | Mastri et al. |
| 5,779,718 A | 7/1998 | Green et al. |
| 5,797,934 A | 8/1998 | Rygaard |
| 5,817,113 A | 10/1998 | Gifford, III et al. |
| 5,823,956 A | 10/1998 | Roth et al. |
| 5,827,316 A | 10/1998 | Young et al. |
| 5,829,447 A | 11/1998 | Stevens et al. |
| 5,833,698 A | 11/1998 | Hinchliffe et al. |
| 5,839,639 A | 11/1998 | Sauer et al. |
| 5,855,614 A | 1/1999 | Stevens et al. |
| 5,881,943 A | 3/1999 | Heck et al. |
| 5,891,160 A | 4/1999 | Williamson, IV et al. |
| 5,904,697 A | 5/1999 | Gifford, III et al. |
| 5,916,226 A | 6/1999 | Tozzi |
| 5,944,730 A | 8/1999 | Nobles et al. |
| 5,944,736 A | 8/1999 | Taylor et al. |
| 5,947,363 A | 9/1999 | Bolduc et al. |
| 5,951,576 A | 9/1999 | Wakabayashi |
| 5,957,363 A | 9/1999 | Heck |
| 5,957,879 A | 9/1999 | Roberts et al. |
| 5,961,481 A | 10/1999 | Sterman et al. |
| 5,964,782 A | 10/1999 | Lafontaine et al. |
| 5,971,973 A | 10/1999 | Peters |
| 5,972,030 A | 10/1999 | Garrison et al. |
| 5,976,159 A | 11/1999 | Bolduc et al. |
| 5,993,464 A | 11/1999 | Knodel |
| 5,993,468 A | 11/1999 | Rygaard |
| 6,015,416 A | 1/2000 | Stefanchik et al. |
| 6,024,748 A | 2/2000 | Manzo et al. |
| 6,030,395 A | 2/2000 | Nash et al. |
| 6,036,705 A | 3/2000 | Nash et al. |
| 6,056,762 A | 5/2000 | Nash et al. |
| 6,066,144 A | 5/2000 | Wolf et al. |
| 6,080,173 A | 6/2000 | Williamson, IV et al. |
| 6,083,234 A | 7/2000 | Nicholas et al. |
| 6,110,187 A | 8/2000 | Donlon |
| 6,131,789 A | 10/2000 | Schulze et al. |
| 6,171,319 B1 | 1/2001 | Nobles et al. |
| 6,171,321 B1 | 1/2001 | Gifford, III et al. |
| 6,176,413 B1 | 1/2001 | Heck et al. |
| 6,176,864 B1 | 1/2001 | Chapman |
| 6,183,486 B1 | 2/2001 | Snow et al. |
| 6,187,019 B1 | 2/2001 | Stefanchik et al. |
| 6,187,020 B1 | 2/2001 | Zegdi et al. |
| 6,187,022 B1 | 2/2001 | Alexander, Jr. et al. |
| 6,190,397 B1 | 2/2001 | Spence et al. |
| 6,190,590 B1 | 2/2001 | Randall et al. |
| 6,193,734 B1 | 2/2001 | Bolduc et al. |
| 6,197,042 B1 | 3/2001 | Ginn et al. |
| 6,206,913 B1 | 3/2001 | Yencho et al. |
| 6,231,506 B1 | 5/2001 | Hu et al. |

| | | |
|---|---|---|
| 6,234,995 B1 | 5/2001 | Peacock, III |
| 6,241,741 B1 | 6/2001 | Duhaylongsod et al. |
| 6,241,742 B1 | 6/2001 | Spence et al. |
| 6,241,743 B1 | 6/2001 | Levin et al. |
| 6,248,117 B1 | 6/2001 | Blatter |
| 6,253,984 B1 | 7/2001 | Heck et al. |
| 6,254,615 B1 | 7/2001 | Bolduc et al. |
| 6,254,917 B1 | 7/2001 | Spence et al. |
| 6,280,460 B1 | 8/2001 | Bolduc et al. |
| 6,332,468 B1 | 12/2001 | Benetti |
| 6,338,712 B2 | 1/2002 | Spence et al. |
| 6,346,074 B1 | 2/2002 | Roth |
| 6,350,252 B2 | 2/2002 | Ray et al. |
| 6,361,543 B1 | 3/2002 | Chin et al. |
| 6,371,965 B2 | 4/2002 | Gifford, III et al. |
| 6,387,105 B1 | 5/2002 | Gifford, III et al. |
| 6,391,039 B1 | 5/2002 | Nicholas et al. |
| 6,401,721 B1 | 6/2002 | Maginot |
| 6,440,146 B2 | 8/2002 | Nicholas et al. |
| 6,443,965 B1 | 9/2002 | Gifford, III et al. |
| 6,450,390 B2 | 9/2002 | Heck et al. |
| 6,451,034 B1 | 9/2002 | Gifford, III et al. |
| 6,461,365 B2 | 10/2002 | Bolduc et al. |
| 6,471,713 B1 | 10/2002 | Vargas et al. |
| 6,562,037 B2 | 5/2003 | Paton et al. |
| 6,726,697 B2 | 4/2004 | Nicholas et al. |
| 6,769,594 B2 | 8/2004 | Orban, III |

FOREIGN PATENT DOCUMENTS

| | | |
|---|---|---|
| EP | 594004 A1 | 4/1994 |
| EP | 643946 A | 3/1995 |
| EP | 656191 A2 | 6/1995 |
| EP | 820725 B1 | 7/1997 |
| EP | 820724 A | 1/1998 |
| EP | 885595 A1 | 12/1998 |
| EP | 1088519 A | 4/2001 |
| EP | 1088519 A1 | 4/2001 |
| FR | 1518083 | 3/1968 |
| FR | 2777446 | 10/1999 |
| GB | 935490 | 8/1963 |
| WO | WO88/01486 | 3/1988 |
| WO | WO95/15715 | 6/1995 |
| WO | WO95/17127 | 6/1995 |
| WO | WO95/35065 | 12/1995 |
| WO | WO97/40754 | 11/1997 |
| WO | WO99/11178 | 3/1999 |
| WO | WO00/69343 | 11/2000 |
| WO | WO01/52748 | 7/2001 |

OTHER PUBLICATIONS

EPO 0120262, International Search Report dated Dec. 20, 2000.
EPO 97112634, International Search Report dated Dec. 18, 1997.
EPO 98110977, International Search Report dated Sep. 25, 1998.
EPO 99118064, International Search Report dated Nov. 1, 2000.
PCT/US01/02043, International Search Report dated Jul. 2, 2001.
PCT/US02/00345, International Search Report dated May 24, 2002.
PCT/US03/18295, International Search Report.
International Search Report—EPO 0120262.
International Search Report—EPO 97112634.
International Search Report—EPO 98110977.
International Search Report—EPO 99118064.
International Search Report—PCT/US01/02043.
International Search Report PCT/US02/00345.
Information Booklet for: LIGACLIP, Ligating Clips, Appliers & Removers For security in Ligation, Ethicon, Inc., 1982.
Information Booklet for: Deep Surgery Advantage-Dramatic New Access Plus Automatic-Feed in Vessel Ligation, Hemoclip ® automatic ligating clip system, Edward Weck & Company, Inc.Sep. 1996.
Information Booklet for: Auto Sutrue® Premium Surgliclip™ Titanium disposable automatic clip appliers, United States Surgical Corporation, 1981.

* cited by examiner

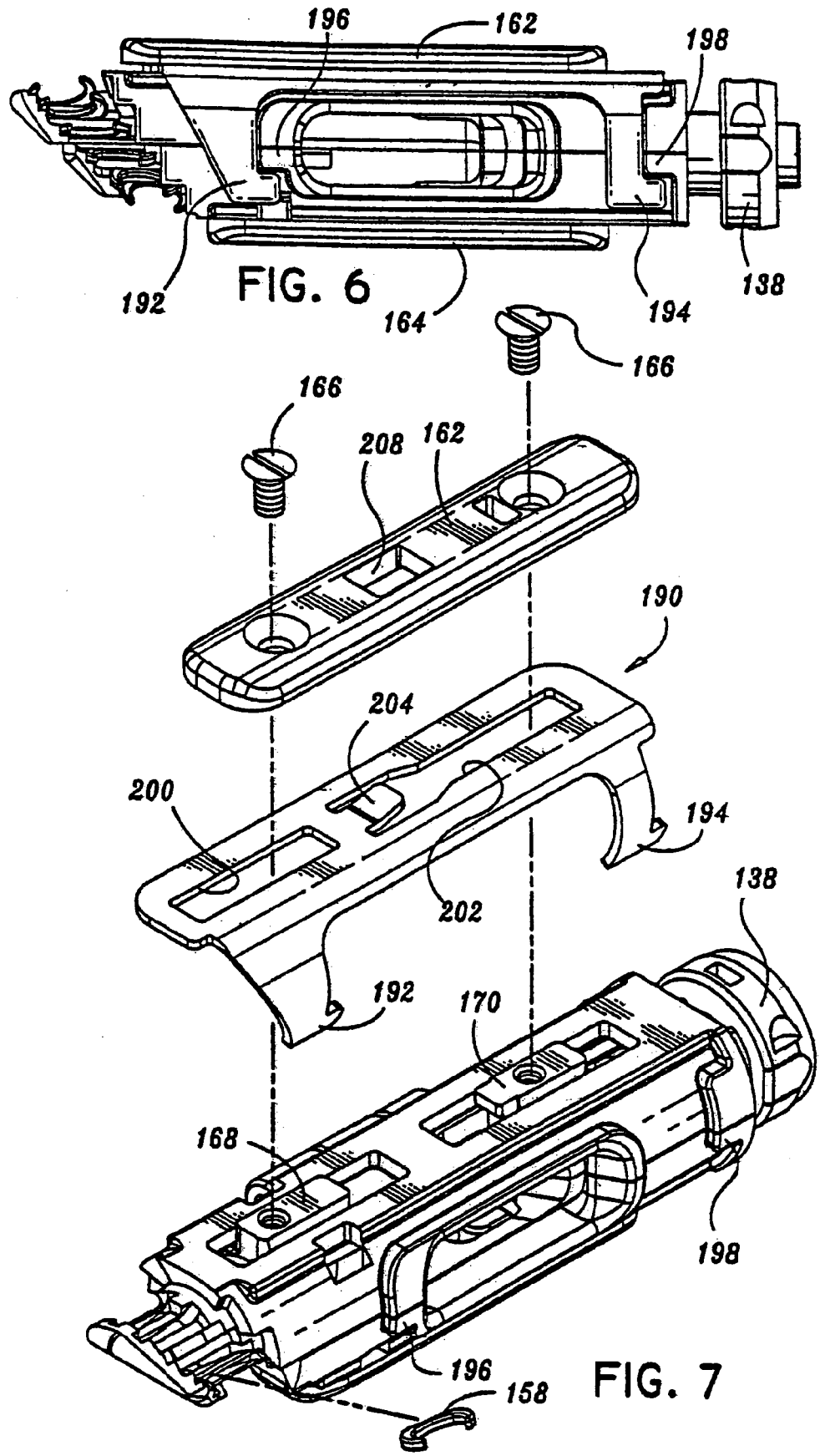

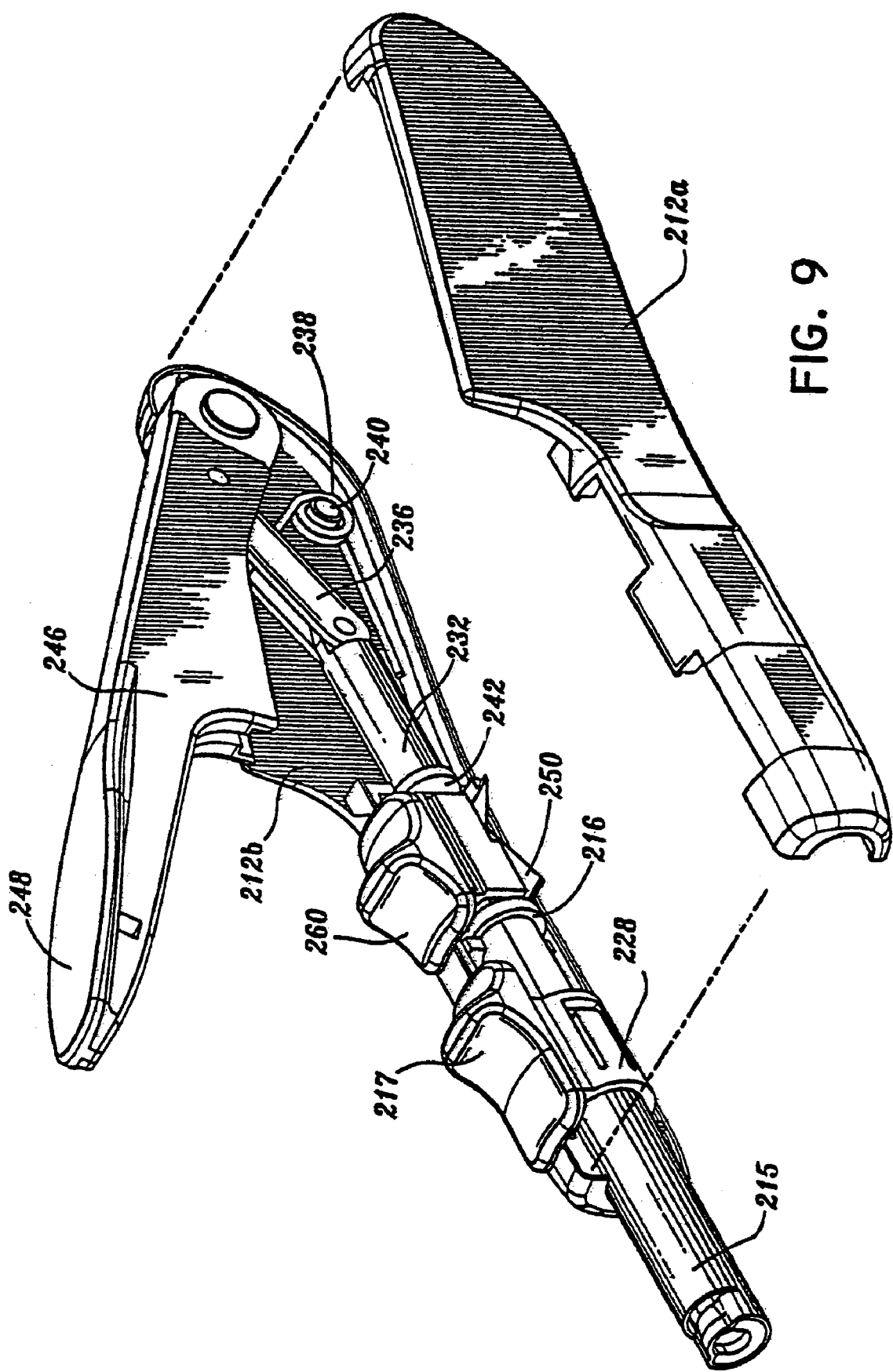

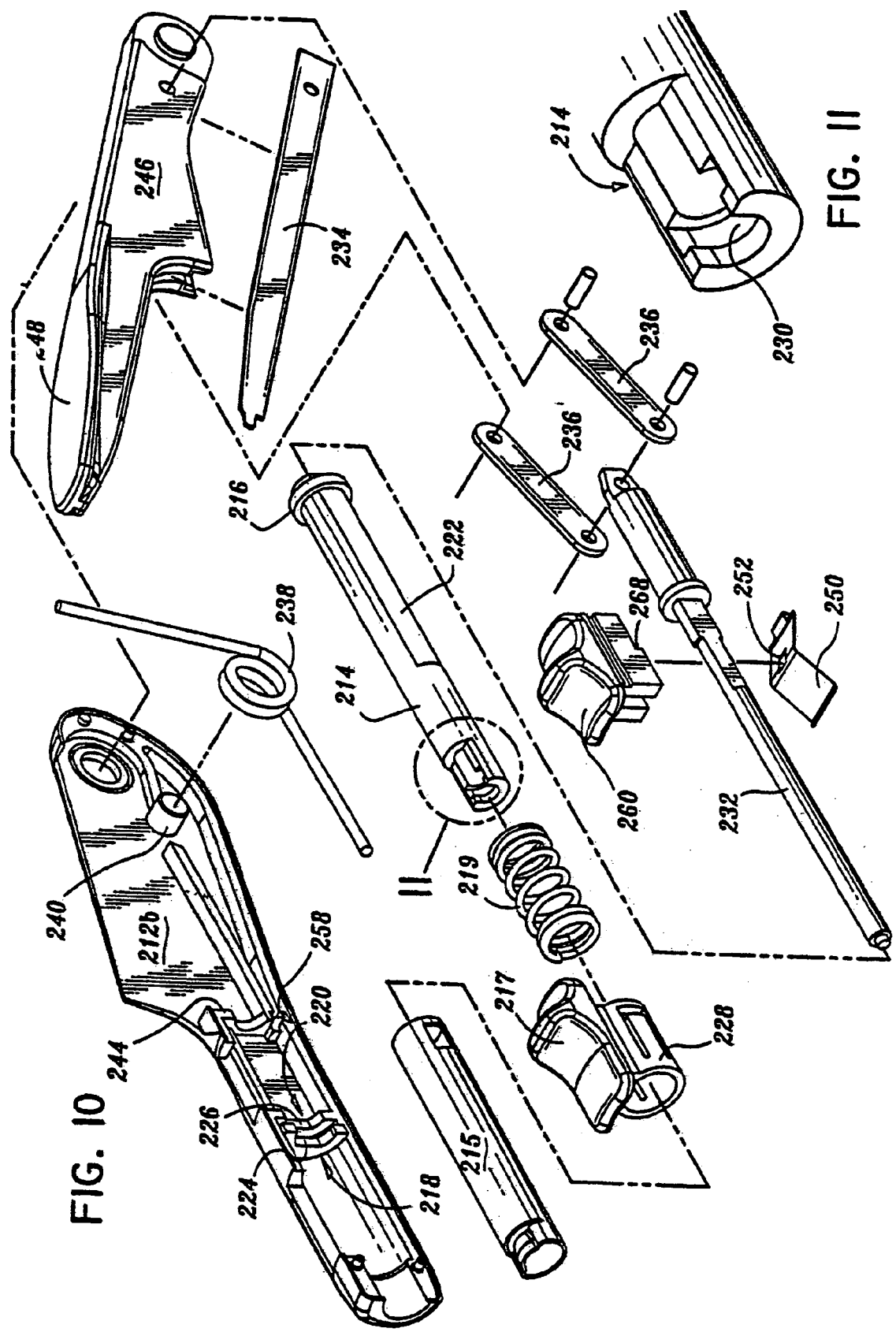

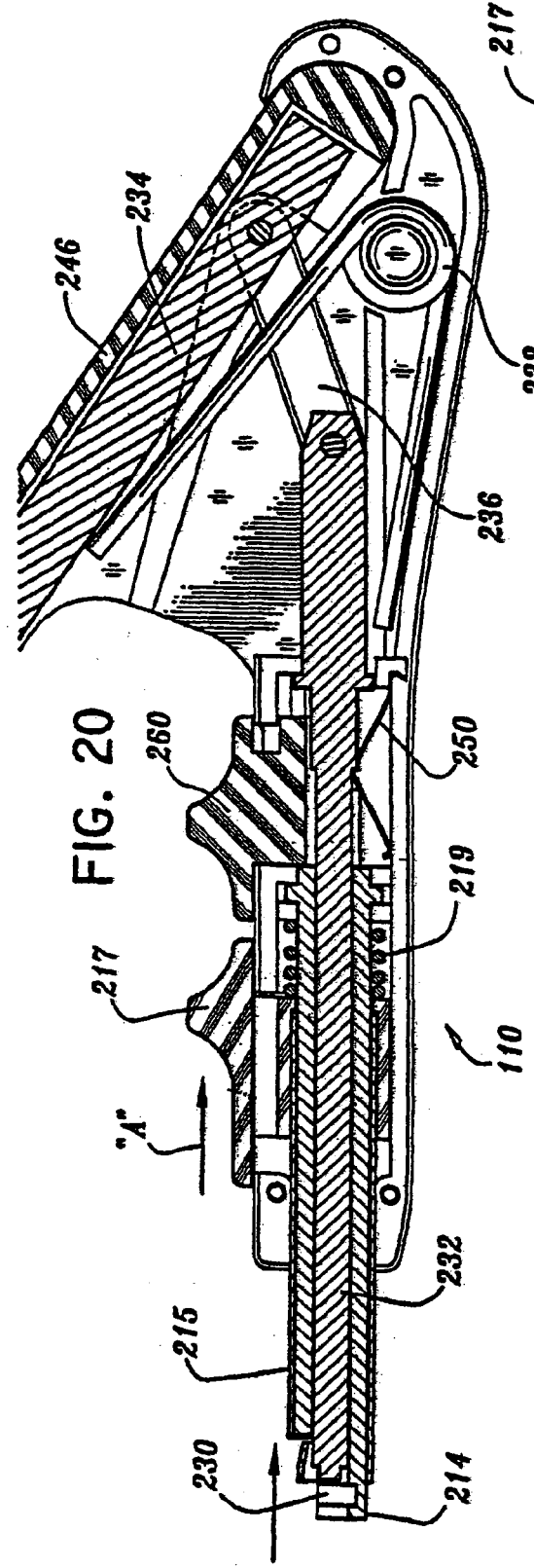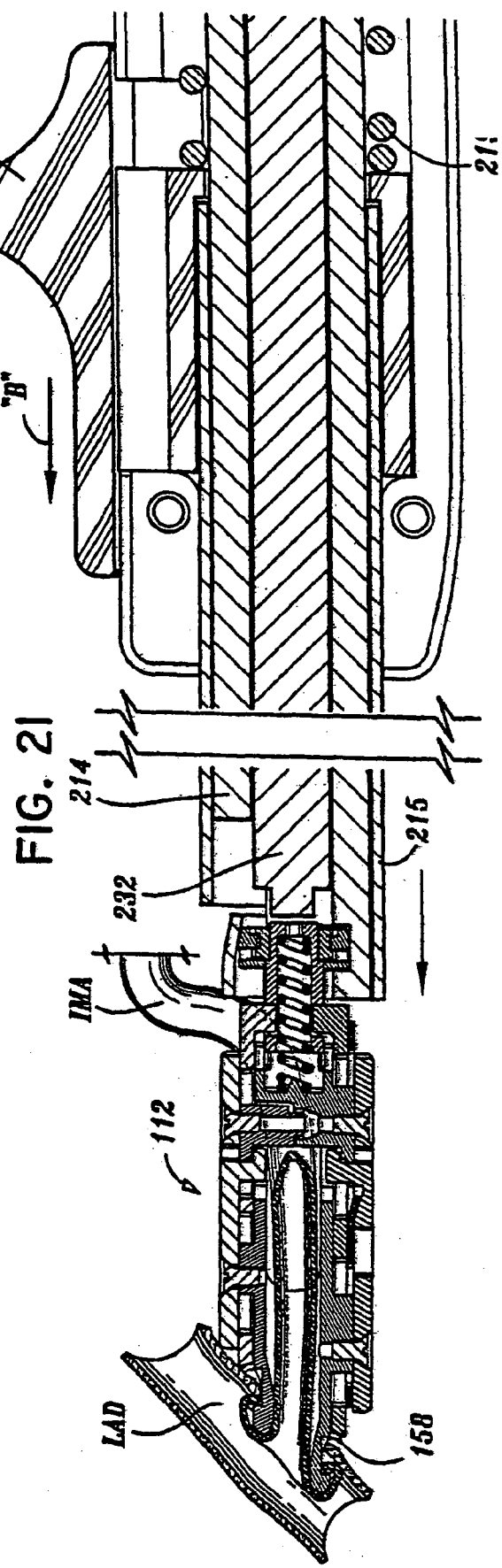

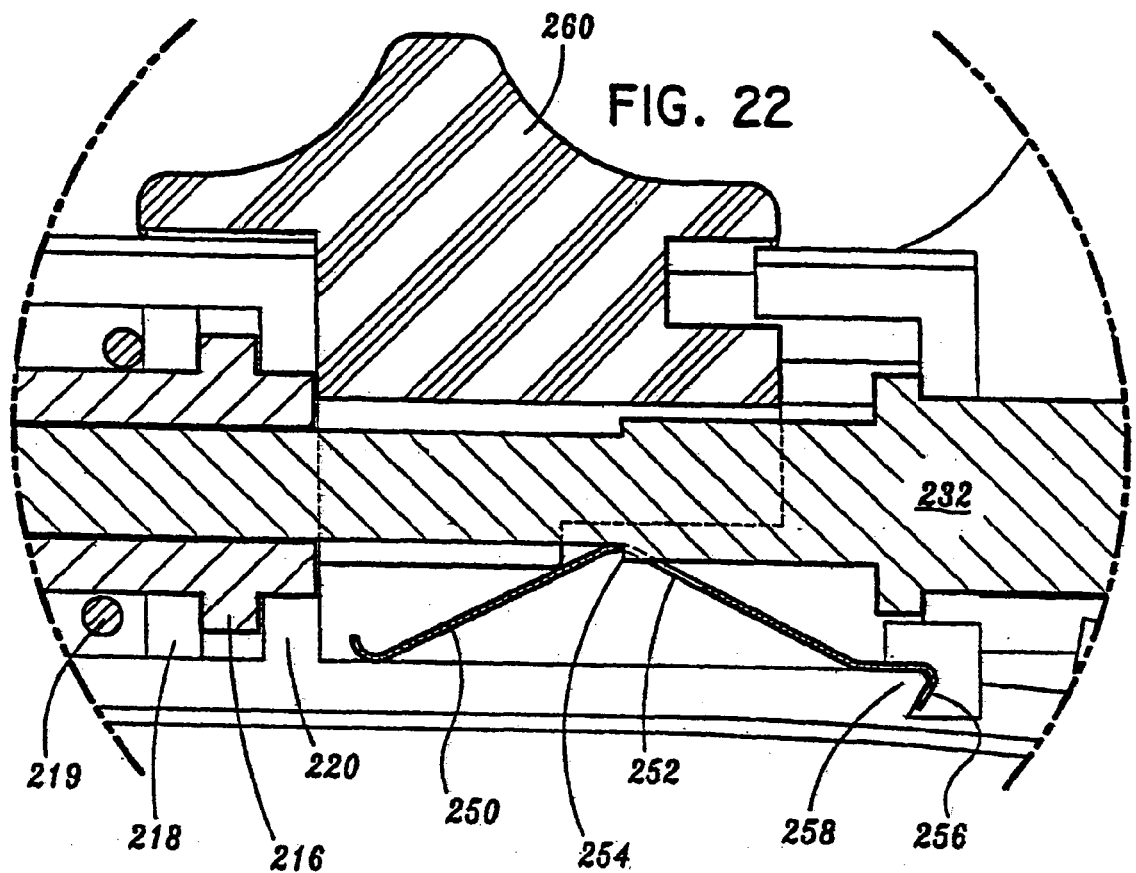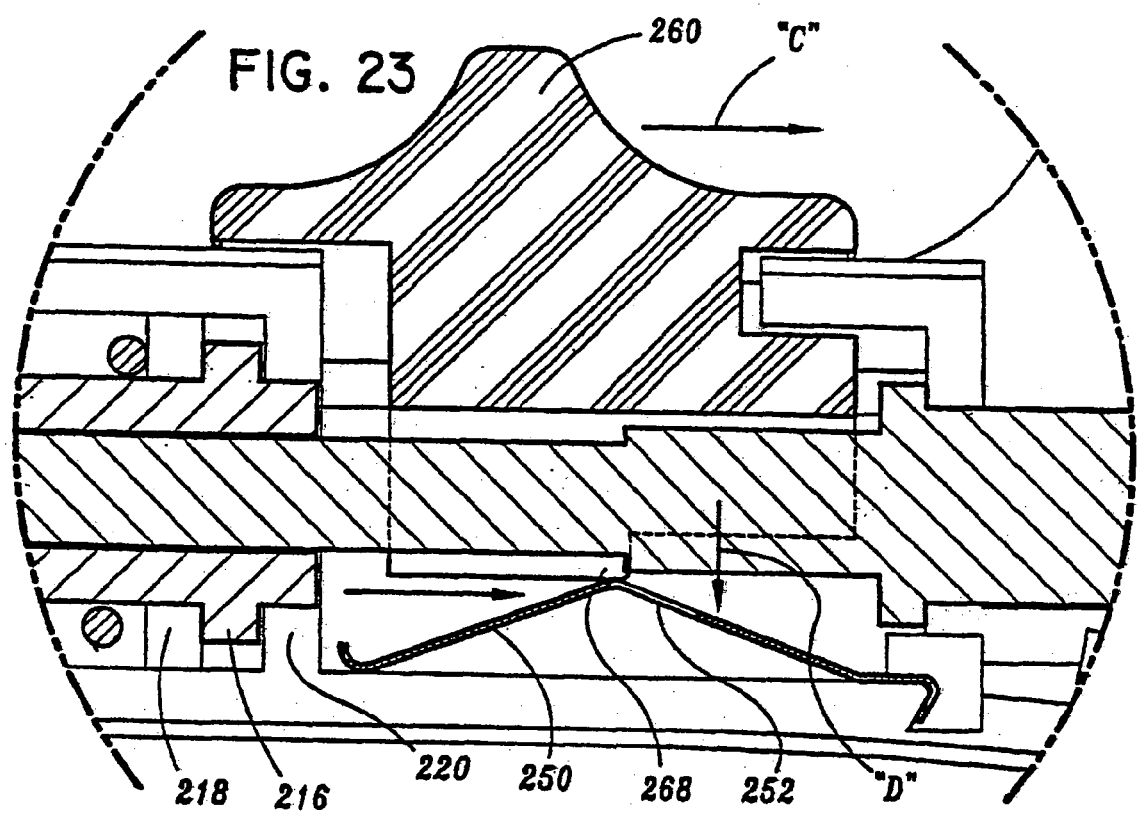

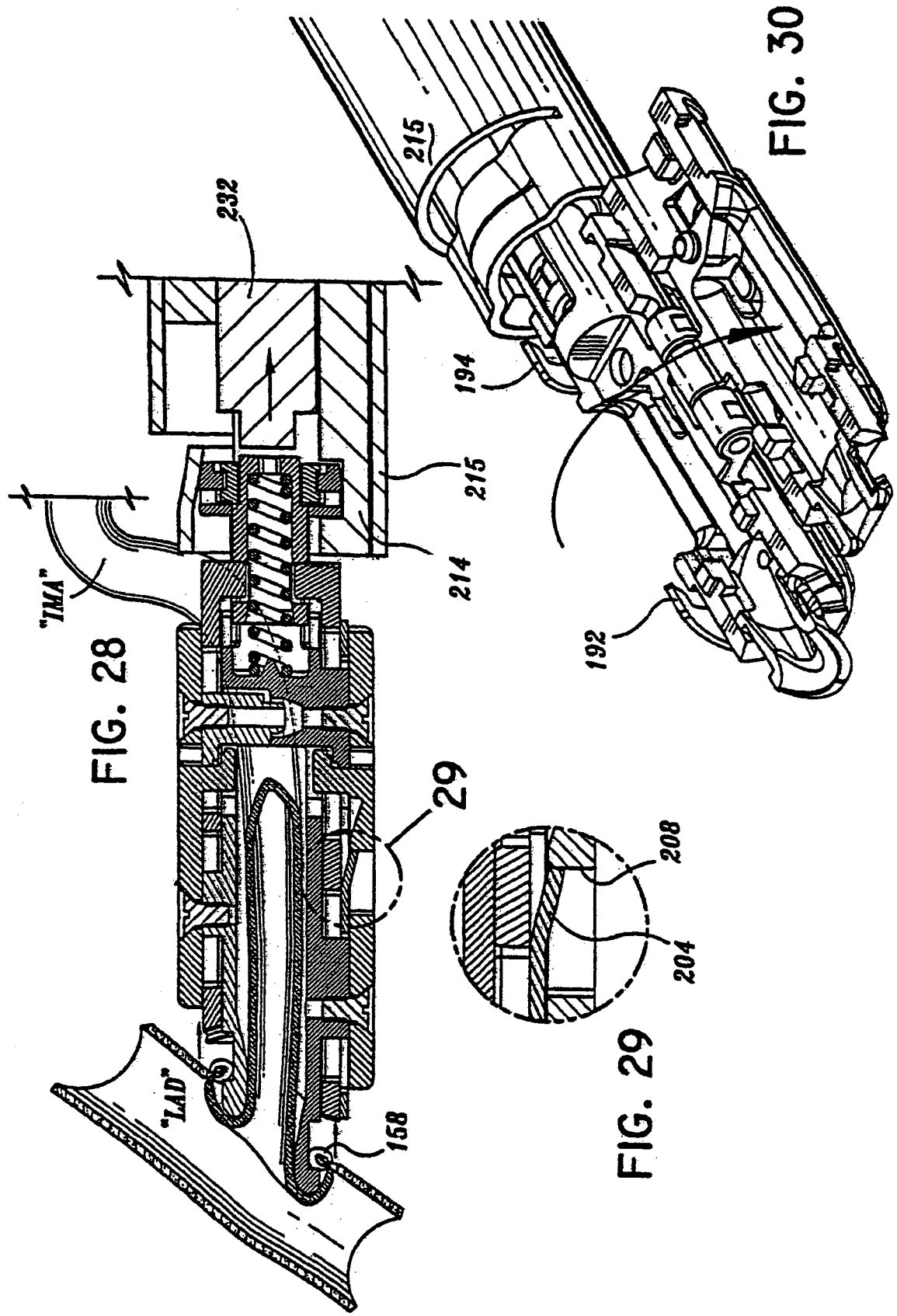

ANASTOMOSIS INSTRUMENT AND METHOD

IN THE CROSS REFERENCE TO RELATED APPLICATION

This application is a continuation of U.S. application Ser. No. 10/191,599 filed on Jul. 8, 2002 now U.S. Pat. No. 6,726,697 by Nicholas et al. which is a continuation of U.S. patent application Ser. No. 09/875,411, now U.S. Pat. No. 6,440,146, filed on Jun. 6, 2001 by Nicholas et al. which is a continuation of U.S. application Ser. No. 09/584,541, now U.S. Pat. No. 6,391,039, filed on Jun. 1, 2000 by Nicholas et al. which is a continuation of U.S. patent application Ser. No. 09/256,260, now U.S. Pat. No. 6,083,234, filed on Feb. 23, 1999 by Nicholas et al. which is a continuation-in-part of U.S. application Ser. No. 08/877,701 now U.S. Pat. No. 6,024,748 filed Jun. 17, 1997 by Manzo et al., which application is a continuation-in-part of U.S. application Ser. No. 08/685,385 filed Jul. 23, 1996 by Hinchliffe et al., now U.S. Pat. No. 5,707,380 which claims priority from U.S. Provisional Application Ser. No. 60/102,326 which was filed on Sep. 28, 1998, the contents of all of the above applications being hereby incorporated by reference herein.

BACKGROUND

1. Technical Field

The present disclosure relates to a surgical instrument and method for performing anastomosis of tubular body structures, and more particularly to an instrument for performing vascular anastomoses.

2. Background of Related Art

Anastomoses of tubular body structures may be performed for a number of different procedures. One general example of an anastomosis is a vascular anastomosis wherein two blood vessels are joined together to permit blood flow therebetween. A specific example of vascular anastomosis is an arteriovenous fistula ("A-V fistula") which is performed to facilitate hemodialysis for end stage kidney disease. The procedure usually consists of an end to side anastomosis joining an artery and a vein in the forearm, e.g., joining the radial artery end to side with the cephalic (radial) vein or the ulnar artery with the basilic (ulnar) vein. It can also be performed in the leg, but usually after all the arm sites have been exhausted. The A-V fistula allows a single puncture at the dialysis unit for blood cleansing. The fistula allows a greater flow and outflow rate through the dialyzer.

Another specific example of a vascular anastomosis is a coronary artery bypass graft ("CABG"). Coronary artery disease is often characterized by lesions or occlusions in the coronary arteries which may result in inadequate blood flow to the myocardium, or myocardial ischemia, which is typically responsible for such complications as angina pectoris, necrosis of cardiac tissue (myocardial infarction), and sudden death. In some cases, coronary artery disease may be treated by the use of drugs and by modifications in behavior and diet. In other cases, dilatation of coronary arteries may be achieved by such procedures as angioplasty, laser ablation, atherectomy, catheterization, and intravascular stents.

For certain patients, a CABG procedure is the preferred form of treatment to relieve symptoms and often increase life expectancy. A CABG procedure consists of direct anastomosis of a vessel segment to one or more of the coronary arteries. For example, a reversed segment of the saphenous vein may be grafted at one end to the ascending aorta as an arterial blood source and at the other end to a coronary artery at a point beyond the arterial occlusion. Alternatively, the internal mammary artery (IMA) is located in the thoracic cavity adjacent the sternum and is likewise suitable for grafting to a coronary artery, such as the left anterior descending artery (LAD).

The performance of a CABG procedure typically requires access to the heart, blood vessels and associated tissue. Access to the patient's thoracic cavity may be achieved in an open procedure by making a large longitudinal incision in the chest. This procedure, referred to as a median stemotomy, requires a saw or other cutting instrument to cut the sternum and allow two opposing halves of the rib cages to be spread apart. U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extensive and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating "window". The retractor includes a rigid frame and a translation frame slidably connected to the rigid frame. Lower and upper blades are rotatably mounted to the rigid frame and the translation frame respectively. The "window" approach enables the surgeon to gain access through a smaller incision and with less displacement of the ribs, and consequently, less trauma to the patient.

Once access to the thoracic cavity has been achieved, surgery on the heart may be performed. Such procedures typically require that the heart beat be arrested while maintaining circulation throughout the rest of the body. Cardioplegic fluid, such as potassium chloride (KCl) is delivered to the blood vessels of the heart to paralyze the myocardium. As disclosed in WO 95/15715 to Sterman et al. for example, cardioplegic fluid is infused into the myocardium through the coronary arteries by a catheter inserted into the ascending aorta. Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is complicated procedure requiring that the desired vessels be properly located and accessed. The progression of the guide wires and catheters must be closely monitored to determine proper placement. Furthermore, the introduction of catheters forms punctures in the blood vessels that must be subsequently closed, and there is an increased risk of trauma to the interior walls of the vessels in which the catheters must pass.

Alternatively, the CABG procedure may be performed while the heart is permitted to beat. Such a procedure is now commonly referred to as minimally invasive direct coronary artery bypass (MIDCAB). A surgical instrument is used to stabilize the heart and restrict blood flow through the coronary artery during the graft procedure. Special care must be given to procedures performed on a beating heart, e.g. synchronizing procedures to occur at certain stages in the cardiac cycle, such as between heartbeats.

To perform a CABG procedure, the harvested vessel segment, such as the IMA, is grafted to the coronary artery by end-to-side anastomosis. Typically, sutures are used to graft the vessel segments. However, conventional suturing is complicated by the use of minimally invasive procedures, such as the window approach. Limited access and reduced visibility may impede the surgeon's ability to manually apply sutures to a graft. Additionally, it is difficult and time consuming to manually suture if the CABG procedure is being performed while the heart is beating as the suturing must be synchronized with the heart beat.

The process of manually suturing the harvested vessel segment to a coronary artery is time consuming and requires a great deal of skill on the part of the surgeon. The resulting sutured anastomosis will also be dependent on the skills of the surgeon. In minimally invasive procedures such as in MIDCAB, the ability to suture is even more complicated due to limited maneuverability and reduced visibility. U.S. Pat. No. 5,707,380 to which issued on Jan. 3, 1998 to Hinchliffe et al., the entire contents of which are hereby incorporated by reference, discloses an apparatus and a procedure that enables the remote anastomosis without piercing of vessels during both conventional and minimally invasive procedures. A continuing need exists, however, for improved surgical instruments and methods for performing remote anastomoses during both conventional and minimally invasive procedures.

SUMMARY

The present disclosure provides a surgical instrument for performing an anastomosis and includes a housing having proximal and distal ends with a shaft extending from the distal end of the housing. The surgical instrument also includes an actuator attached to the housing and a disposable loading unit configured for selective attachment to the shaft.

The disposable loading unit includes a fastener support member configured and dimensioned to support an array of surgical fasteners and a fastener pusher member which is movable through a firing stroke in response to movement of the actuator to deform the surgical fasteners. Preferably, the disposable loading unit includes opposed split sections which are pivotable relative to one another between an open position and a close position after movement of the fastener pusher member through the firing stroke.

In one embodiment, the opposed split sections of the disposable loading unit are locked in a closed, non-pivotable configuration prior to initiation of the firing stroke. In another embodiment, the return of the fastener pusher member unlocks the opposable split sections to allow pivotable movement thereof.

In another embodiment according to the present disclosure, the fastener support member supports generally C-shaped surgical fasteners in a partially compressed configuration. Preferably, each of the surgical fasteners includes a proximal tip and a distal tip and at least one of the proximal and distal tips of at least one of the surgical fasteners is atraumatic.

The present disclosure also relates to a method of performing a vascular anastomosis between first and second vessels and includes the steps of providing a surgical instrument which includes:
 a housing having proximal and distal ends with a shaft extending from the distal end of the housing;
 an actuator attached to the housing;
 a disposable loading unit configured for selective attachment to the shaft, the disposable loading unit having a passageway defined therethrough. The disposable loading unit includes a fastener support member configured and dimensioned to support an array of surgical fasteners at a distal end thereof and a fastener pusher member which is movable through a firing stroke in response to movement of the actuator to deform the surgical fasteners.

The method further includes the step of inserting the first vessel through the passageway and everting an end of the first vessel over the distal end of the fastener support member adjacent the distal tips of the surgical fasteners. An additional step of the method include inserting the fastener support member and the everted end of the first vessel into an opening in a sidewall of the second vessel such that the proximal tips of the surgical fasteners are adjacent the opening. The method also includes the steps of connecting the disposable loading unit to the shaft and actuating the actuator to deform the surgical fasteners to secure the first and second vessels in fluid communication with one another.

BRIEF DESCRIPTION OF THE DRAWINGS

An illustrative embodiment of the subject surgical instrument and method are described herein with reference to the drawings wherein:

FIG. 6 is a side view of the disposable loading unit of the embodiment of FIG. 2;

FIG. 7 is a perspective view of the disposable loading unit of the embodiment of FIG. 2 showing a hinge lock and a cover plate separated;

FIG. 9 is a perspective view of a handle/actuator assembly of the surgical instrument with parts separated;

FIG. 10 is a perspective view of the handle/actuator assembly of FIG. 9 shown with parts separated;

FIG. 11 is an enlarged view of the distal end of a disposable loading unit holding tube;

FIG. 20 is a horizontal cross-sectional view of the handle/actuator assembly;

FIG. 21 is a partial horizontal cross-sectional view showing a locking mechanism to secure the disposable loading unit to the handle/actuator assembly;

FIG. 22 is an enlarged view isolating on the safety firing lockout member of the handle/actuator assembly;

FIG. 23 is a view similar to FIG. 22, which shows operation of the safety firing lockout;

FIG. 28 is a horizontal cross-sectional view, which shows retraction of an actuator rod of the handle/actuator assembly and lockout of a hinge lock on the disposable loading unit;

FIG. 29 is an enlarged view of the indicated area of detail of FIG. 28;

FIG. 30 is a perspective view of the distal end of the surgical instrument showing the opening of the disposable loading unit;

DETAILED DESCRIPTION OF PREFERRED EMBODIMENTS

Preferred embodiments of the surgical instrument and method disclosed herein will be described in terms of a minimally invasive direct coronary artery bypass (MID-CAB) procedure wherein a vascular anastomosis is created by joining a section of a harvested vessel, e.g., the internal memory artery (IMA) to bypass an occlusion in a coronary artery, e.g., the left anterior descending artery (LAD). However, the presently disclosed surgical anastomosis instrument may also be utilized in performing anastomosis of other tubular luminal body structures. For example, the presently disclosed surgical anastomosis instrument may also be utilized to perform an A-V fistula to facilitate hemodialysis. This procedure consists of an end-to-side anastomosis joining an artery and a vein in the forearm or near the elbow. The A-V fistula allows a single puncture at the dialysis unit for blood cleansing.

Figure 1:
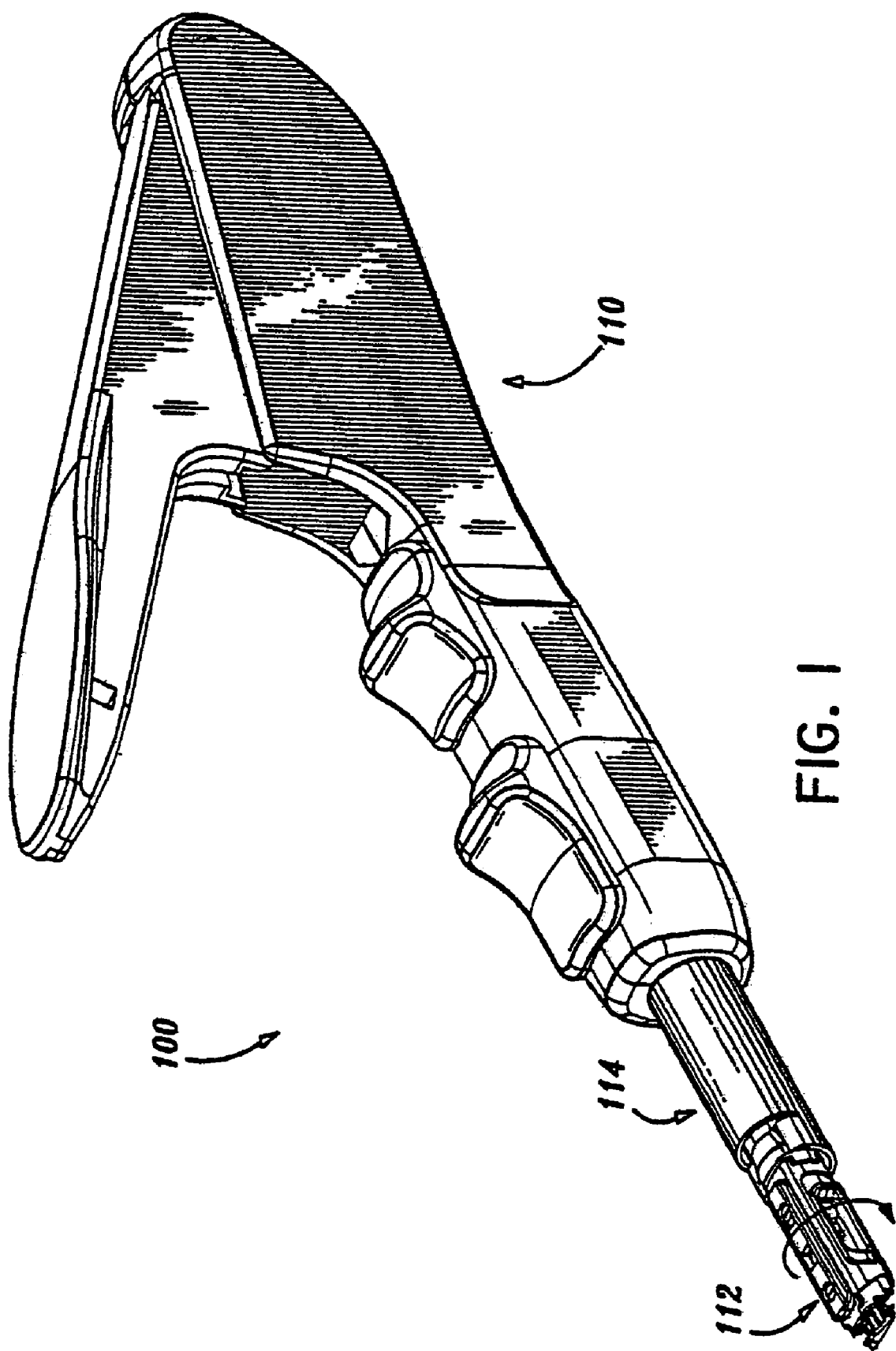
FIG. 1 is a perspective view of a surgical instrument constructed in accordance with a preferred embodiment of the present disclosure.
Figure 2:
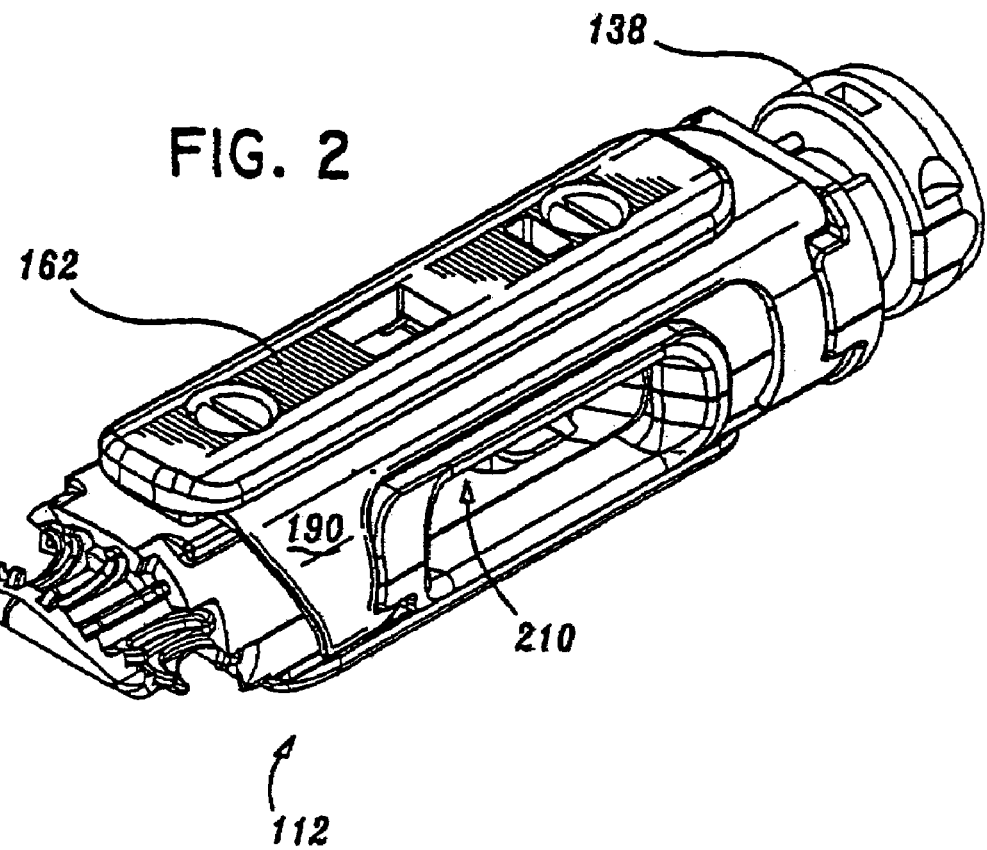
FIG. 2 is a perspective view of a disposable loading unit constructed in accordance with a preferred embodiment of the present disclosure.
Figure 3:
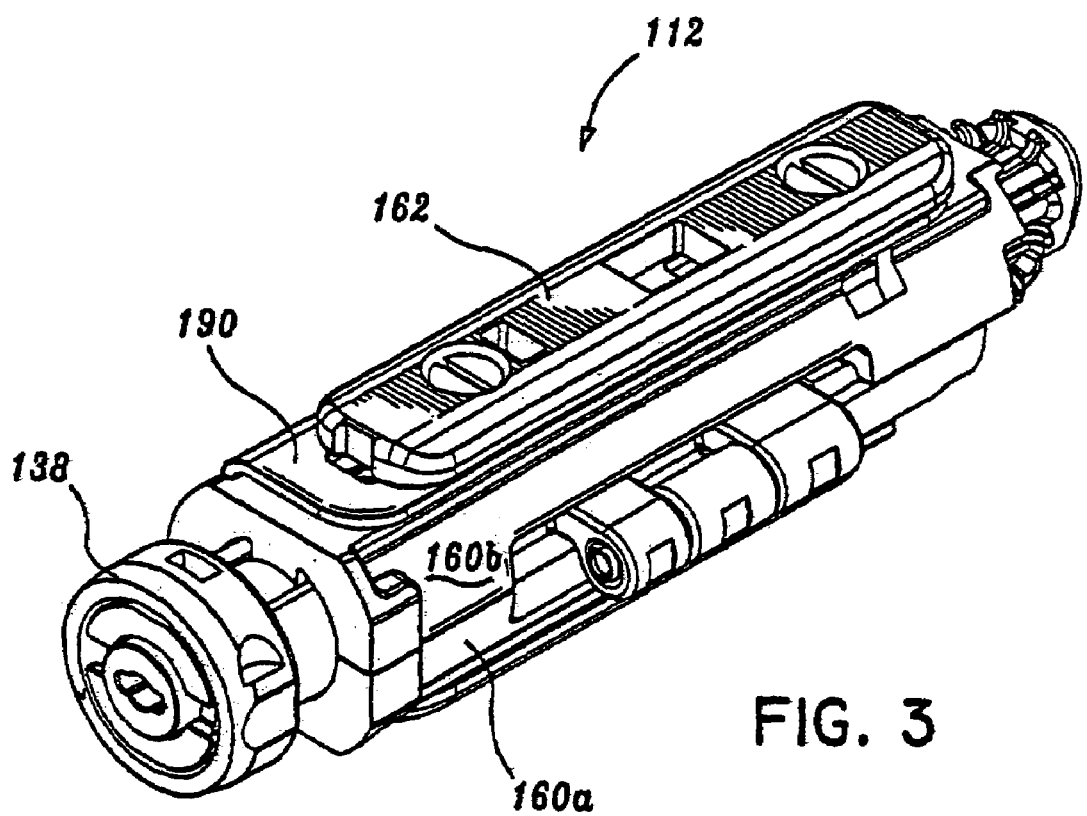
FIG. 3 is a perspective view of the disposable loading unit of FIG. 2 as seen from a reverse angle.
Figures 4, 5:
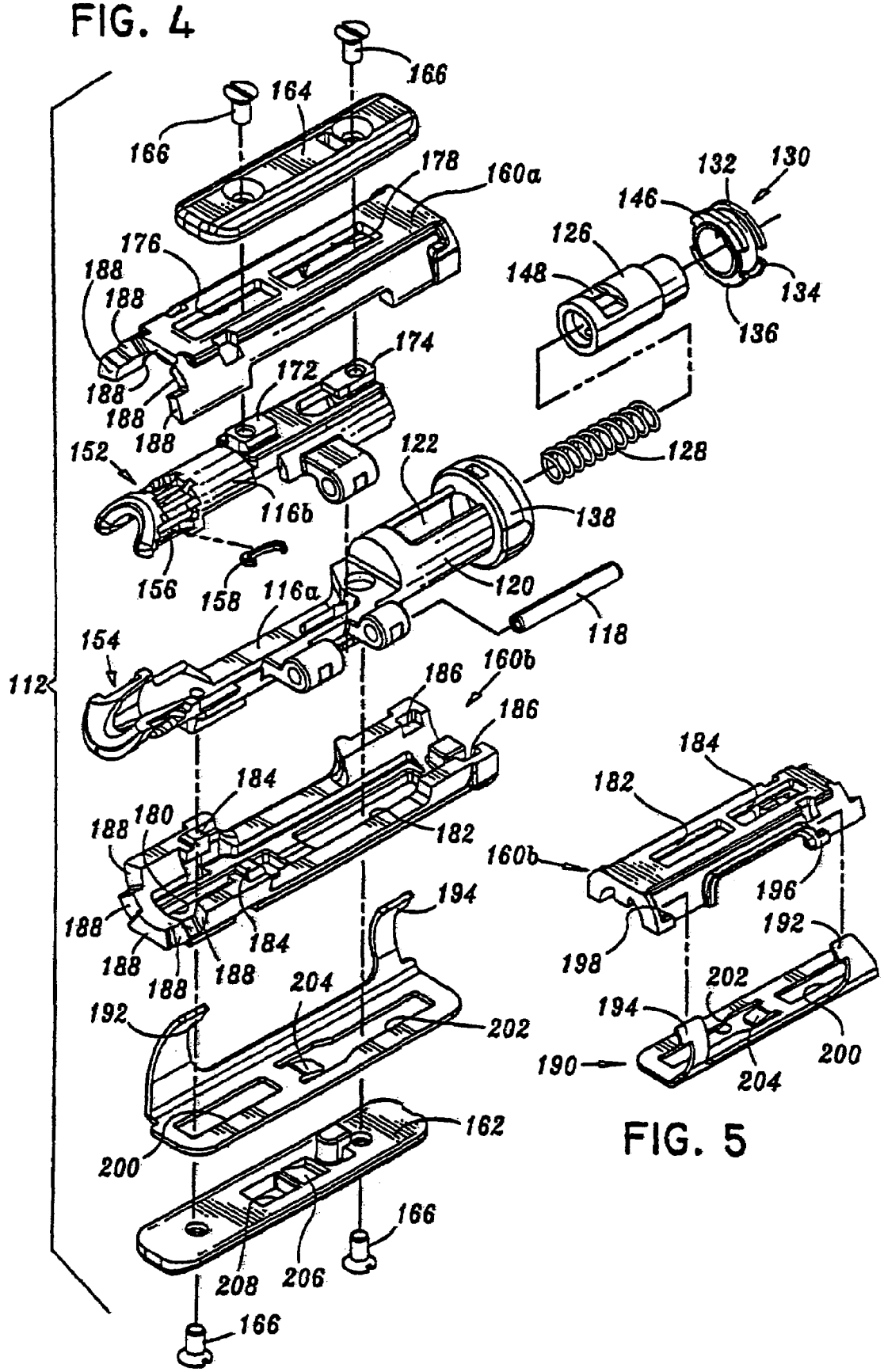
FIG. 4 is a perspective view the disposable loading unit embodiment of FIG. 2 shown with parts separated.
FIG. 5 is a perspective view of a fastener pusher half-section and a hinge lock the embodiment of the disposable loading unit of FIG. 2.

Referring now in detail to the drawing figures in which like reference numerals identify similar or identical elements, one embodiment of the present disclosure is illustrated generally in FIG. 1 and is designated therein as surgical instrument 100. Briefly, surgical instrument 100 includes a handle/actuator assembly 110 having a disposable loading unit 112 which is removably and rotatably attached to the handle/actuator assembly 110 by way of intermediate section 114 which extends from a distal end of housing/actuator assembly 110.

Referring now to FIGS. 2–8, disposable loading unit 112 includes a two-part fastener support member made up of split half-sections 116a and 116b which form a hinge and are connected to each other by hinge pin 118. Split half-section 116a includes an actuator barrel 120 which forms a bore that opens at a proximal end. Actuator barrel 120 includes opposed longitudinal slots 122 and 124 to facilitate operation of an actuator member 126 which is slidably mounted in actuator barrel 120. Actuation member 126 is spring biased to a proximal-most orientation by a coil spring 128. Actuator 126 is further retained within actuator barrel 120 by a lock ring 130 which includes an annular groove 132 defined by proximal and distal flanges 134 and 136, respectively. Each of the proximal and distal flanges 134 and 136 include a pair of opposed slotted portions which are aligned to facilitate locking of ring 130 anterior portion of a mounting hub 138.

Figure 8:
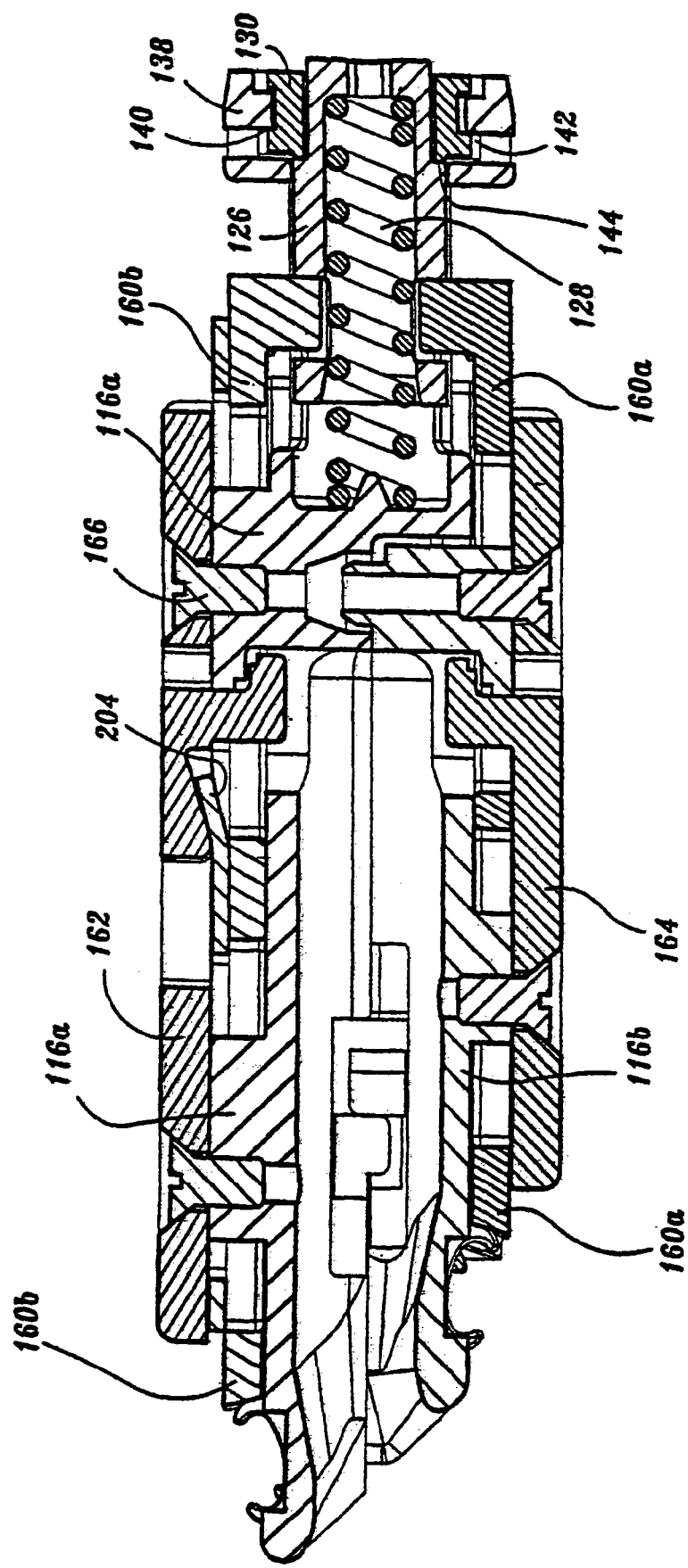
FIG. 8 is a horizontal cross-sectional view of the disposable loading unit shown greatly enlarged for clarity.
Figure 12:
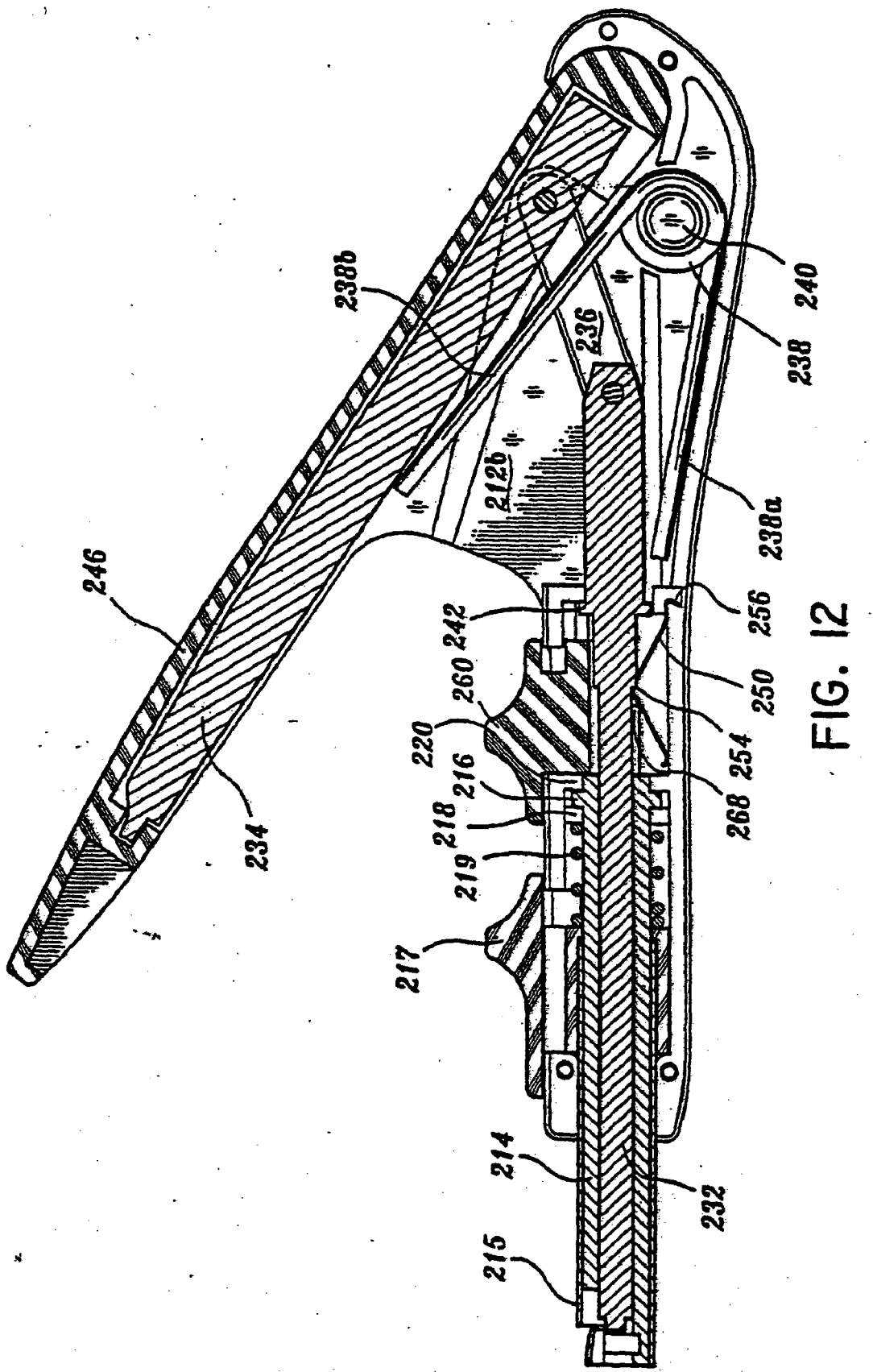
FIG. 12 is a horizontal cross section of the handle/actuator assembly.

For example, by way of passing lock ring 130 over opposed extended tabs 140 and 142, as best seen in FIG. 8, at the rotating lock ring 130 one quarter turn such that the pairs of opposed slots formed in proximal flange and distal flange 134 and 136, respectively, are rotated 90° with respect to tabs 140 and 142. Lock ring 130 is biased against the distal facing surfaces of extended tabs 140 and 142 by the force of compressed coil spring 128 which is disposed in the bore formed longitudinally within actuator 126. In particular, a shoulder portion 144 of actuator 126 is biased against an annular lip 146 (FIG. 4) which is formed on the distal facing surface of lock ring 130. Actuator member 126 further includes a pair of opposed transversely extending slots 148 and 150 formed on the outer surface thereof which, as will be described in further detail herein, provide an engagement surface for a fastener pusher member.

Split half-sections 116a and 116b of the fastener support member are provided with fastener retaining sections 152 and 154. Each of fastener retaining sections 152 and 154 are provided with a plurality of longitudinal channels 156 which are configured and dimensioned to support a "C"-shaped surgical fastener or clip 158 therein by, for example, friction or partial compression of clips 158. Fastener retaining sections 152 and 154 are preferably arranged such that longitudinal channels 156 form an eccentric array radially about the outer surface of fastener support member 116. This arrangement facilitates the efficacious formation of arr angled connection or fistula between the vessels to be joined. Such a connection facilitates better fluid flow through the anastomotic site.

A fastener pusher member 160 is provided to facilitate deformation of clips 158 during firing of the instrument. Fastener pusher member 160 is made up of split half-sections 160a and 160b which are secured to split half-sections 116a and 116b, respectively, by way of mounting plates 162 and 164 and screws 166 which are threaded into threaded holes formed in receiving posts 168, 170; and 172, 174 disposed on split half-sections 116a and 116b, respectively. Mounting plates 162 and 164 are attached to split half-sections 116a and 116b in a manner to permit longitudinal sliding movement of split half-sections 160a and 160b of fastener pusher member 160 relative to fastener support member 116. This sliding movement is facilitated by longitudinally aligned slots 176, 178, and 180, 182 which are provided on split half-sections 160a and 160b, respectively.

Split half-sections 160a and 160b are further provided with molded surfaces such as protrusions 184 and depressions 186 as shown on split half-section 160a which interfit with corresponding protrusions and depressions formed on split half-section 160a so as to prevent relative longitudinal movement of split half-sections 160a and 160b. Stepped camming or pusher surfaces 188 are formed on the distal ends of each of split half-sections 160a and 160b and serve to cam a proximally oriented portion of clips 158 towards a distal oriented portion of clips 158. This motion effects deformation of the clips upon firing of surgical instrument 100.

Finally, a hinge lock 190 is mounted between mounting plate 162 and split half-section 160b. Hinge lock 190 is provided with latch portions 192 and 194 which extend transversely across one side of disposable loading unit 112 to latch onto raised correspondingly shaped surfaces 196 and 198, respectively, formed on the outer surface of split half-section 160a. Hinge lock 190 is further provided with a pair of longitudinally oriented slots 200 and 202 which are radially aligned with slots 180 and 182 of split half-section 160b to facilitate relative longitudinal movement of hinge lock 190 with respect to both split half-section 160b and split half-section 116a.

A flexible return lockout tab 204 extends proximally from the distal end of slot 202 and is cantilevered outwardly away from a plane defined by slots 202 and 204 such that it is positioned in a tab receiving recess 206 formed on the inner surface of mounting plate 162 when the DLU 112 is in a pre-fired condition. A lockout slot 208 is formed longitudinally aligned with tab receiving recess 206 and spaced distally therefrom such that upon distal movement of hinge lock 190 (when split half-section 160b is moved distally), return lockout tab will be deflected to a flattened condition and will extend into lockout slot 208 in order to prevent subsequent proximal movement of hinge lock upon proximal movement of split half-section 160b after firing of surgical instrument 100.

In this manner, after firing of surgical instrument 100, latch portions 192 and 194 of hinge lock 190 will remain distal relative to raised surfaces 196 and 198 of split half-section of 160a by permitting the split half-sectioned DLU 112 to be opened by pivoting split half-sections 116b and 160a away from split half-sections 116a and 160b to facilitate removal of the vessel segment from within the vessel pathway formed through the distal end of DLU 112 and out through a lateral opening 210 formed by aligned molded recesses formed in each of split half-sections 116a, 116b;

and 160a and 160b of fastener support member 116 and fastener pusher member 160, respectively.

Referring now to FIGS. 9–12, the handle/actuator assembly 110 of surgical instrument 100 will now be described in detail. Handle/actuator assembly 110 includes a housing formed of half-sections 212a and 212b which are preferably molded to have recessed inner surfaces and contours formed therein to house the various components which are contained within handle/actuator assembly 110. In particular, handle/actuator assembly 110 includes a DLU mounting assembly which facilitates detachable mounting of a DLU 12 to the distal end of handle/actuator assembly 110. The DLU mounting assembly includes an elongated holding tube 214 which is held longitudinally and rotationally fixed relative to housing half-sections 212a and 212b. This mounting arrangement may be accomplished for example, by way of an annular flange 216 formed adjacent the proximal end of holding tube 214 being held within an annular groove defined by partition wall segments 218 and 220 formed in each of housing half-sections 212a and 212b.

Holding tube 214 is further prevented from rotational movement by way of flattened sidewall portions 222 formed on opposing sides of holding tube 214 being retained within and abutting flat surfaces 224 and 226 formed long partition wall segments 218 and 220, respectively, in each of housing half-sections 212a and 212b. DLU locking tube 215 is secured within a collar 228 formed on slide 217. Tube 215 may be secured in slide 217 by any suitable means, for example, friction fitting bonding, adhesives, or the like.

Coil spring 219 is interposed in housing half-sections 212a and 212b between partitioned segments 218 and the proximal end surface of collar 228. In this manner, locking tube 215 is biased in a distal-most position which corresponds to a locked position to retain DLU 112 on the distal end of surgical instrument 100. The distal end of DLU holding tube 214 is provided with a semi-annular groove 230 which is dimensioned to receive mounting hub 138 formed at the proximal end of DLU 112. Semi-annular groove 230 is dimensioned to permit DLU mounting hub 138 to rotate within the groove.

Handle and actuator assembly 110 further includes a firing assembly which facilitates movement of actuator 126 housed within the actuator barrel 120. In the embodiment illustrated in FIGS. 9–15, the firing assembly is a linkage mechanism which imparts reciprocating longitudinal movement in an actuator rod by way of movement of an actuator lever However, it is within the scope of the present disclosure that the actuator rod may be reciprocatingly moved by any suitable known methods. The firing assembly basically includes an actuator rod 232 which is connected to an actuator lever 234 by way of links 236 pivotally attached at either end to actuator rod 232 and actuator lever 234, respectively.

Actuator rod 232 is slidably disposed within a longitudinal bore formed through DLU holding tube 214. Actuator rod 232 is biased in a proximal-most position by way of a torsion spring 238 being mounted on a post 240 formed near the proximal end of housing half-section 212b. Extended legs 238a and 238b are provided on torsion spring 238 to bias actuator lever 234 upwardly away from housing half-sections 212a and 212b thereby pulling actuator rod 232 toward its proximal-most position as determined by the abutment of annular shoulder 242 against partition 244 formed in each of housing half-sections 212a and 212b.

To facilitate comfort and ease of operation for the user, a cover 246 is secured over actuator lever 234 and is independently pivotally mounted to housing half-sections 212a and 212b. Cover 246 is provided with an ergonomic surface 248 which is contoured and configured to be comfortably actuated by the thumb of a user when handle and actuator assembly 210 is held in the palm of the user's hand.

A firing safety mechanism is also provided to prevent premature firing of surgical instrument 100. In the illustrated embodiment, the firing safety assembly includes an inverted leaf spring 250 having a cut-out portion 252 formed therein which biases against a shoulder 254 formed on actuator rod 232. Spring 250 is further provided with a hook portion 256 formed at the proximal end thereof which latches onto a protruding surface 258 formed in housing half-sections 212a and 212b. In this manner, spring 250 prevents distal movement of actuator rod 232 when the safety mechanism is armed.

A safety release slide 260 which includes an upwardly extending contact surface is exposed from the upper surface of housing half-sections 212a and 212b to permit the user to operate the slide and forms a clevis on a lower portion thereof which receives a flattened section 266 of actuator rod 332. Safety release slide 260 is further provided with a camming surface 268 along the lower edge thereof which cams the spring 250 out of contact with shoulder 254 upon proximal movement of safety release slide 260.

In use, as shown in FIGS. 13–31, surgical instrument 100 facilitates the performance of a vascular anastomosis without the need for manual suturing of the vessels. The method and usage described herein will be addressed in terms of minimally invasive vascular anastomosis performed on a beating heart such as in a MIDCAB procedure. However, the presently disclosed surgical instrument may also be used in performing anastomoses of other tubular or luminal body structures without departing from the scope of the present disclosure. For example, surgical instrument 100 may be used in conventional open CABG procedures using a median sternotomy or other large incision without stopping the heart. Alternatively, the thoracic "window" procedure may be used to achieve access to the heart. The "window" approach involves a smaller incision and less displacement of the ribs, and therefore is less traumatic to the patient. For this approach, conventional surgical techniques are used to determine the location of the incision to access the chest cavity.

Figure 13:
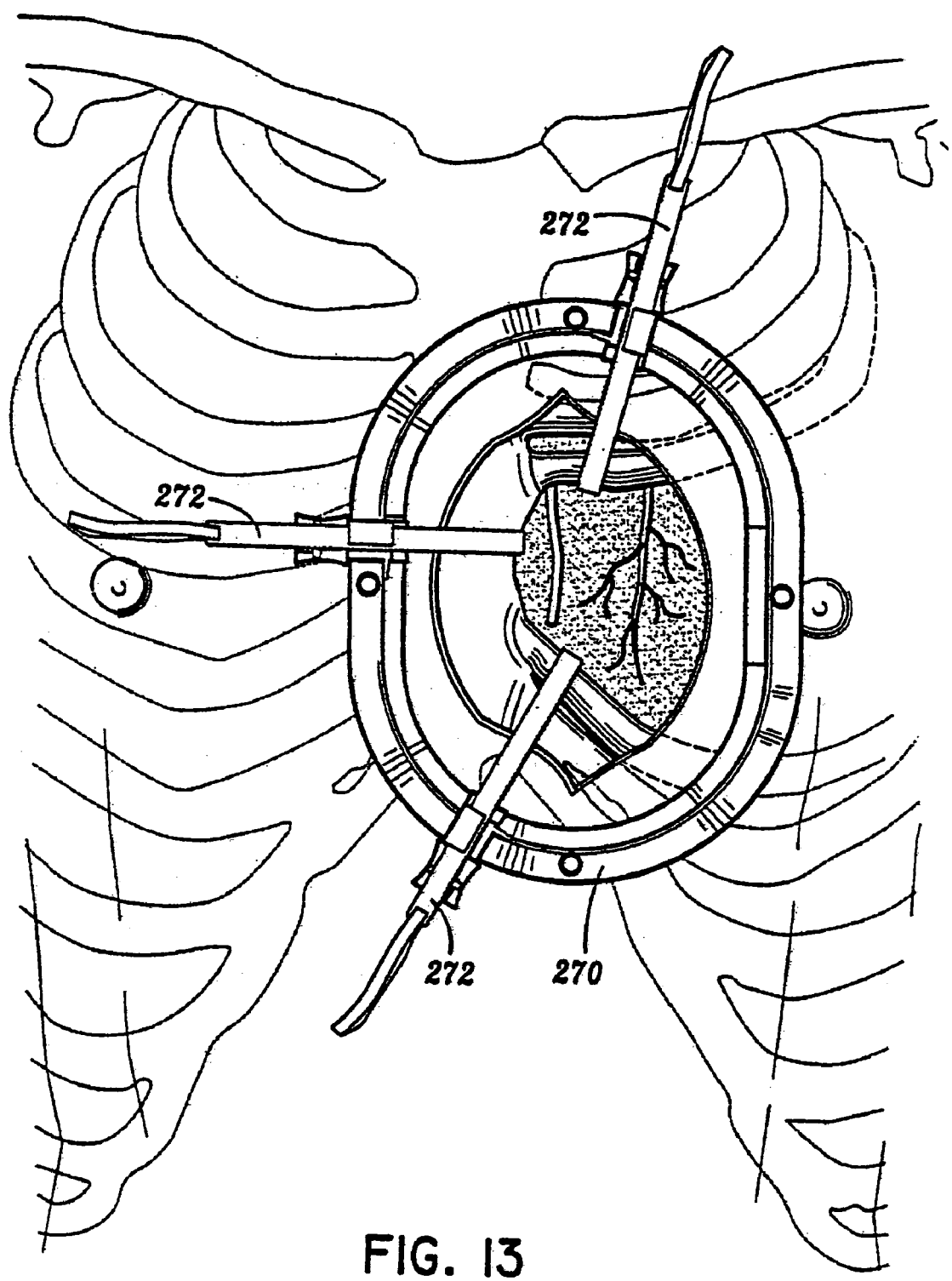
FIG. 13 is a view showing an operating "window" with the patient's heart exposed.

In particular, a surgical retractor assembly may be used to separate the ribs at the site of the incision as shown in FIG. 13. Specifically, a base 270 is placed on the chest of the patient with the central opening defined by the base being positioned over the operative site. Retractor assemblies 272 are mounted to the base at various locations. Each of retractor assemblies 272 includes a blade having a hook to engage either a rib or the sternum therewith. The retractor assemblies are mounted and used to retract ribs until a sufficiently large opening in the chest cavity is defined to provide direct access to the heart. For example, the sternum and the fourth and fifth ribs can be split apart to create a window. Other configurations of spreading the ribs and/or selectively cutting individual ribs away from the sternum may also be utilized for a particular procedure.

Once the desired access to the heart is achieved, the graft vessel, e.g., the internal memory artery (IMA) is dissected from the surrounding cartilage and muscle, in a free end of the vessel is exposed. The occluded coronary artery, e.g., the left anterior descending artery (LAD), is then prepared for receiving the IMA graft. The heart is positioned in the desired orientation either by traction sutures passing through the pericardium or by manipulation with heart manipulation instruments which are held by the surgical personnel or clamped in a fixed orientation to a base such as the retractor assembly base. One such heart manipulating instrument is available from United States Surgical Corporation of Norwalk, Conn. Blood flow through the LAD can be restricted by cardiopulmonary bypass and pericardial cooling. Alternatively, a damping instrument may be applied directly on the LAD to restrict blood flow and reduce movement of the heart near the LAD. Such a heart stabilizing instrument is also available from United States Surgical Corporation of Norwalk, Conn.

Figure 14:
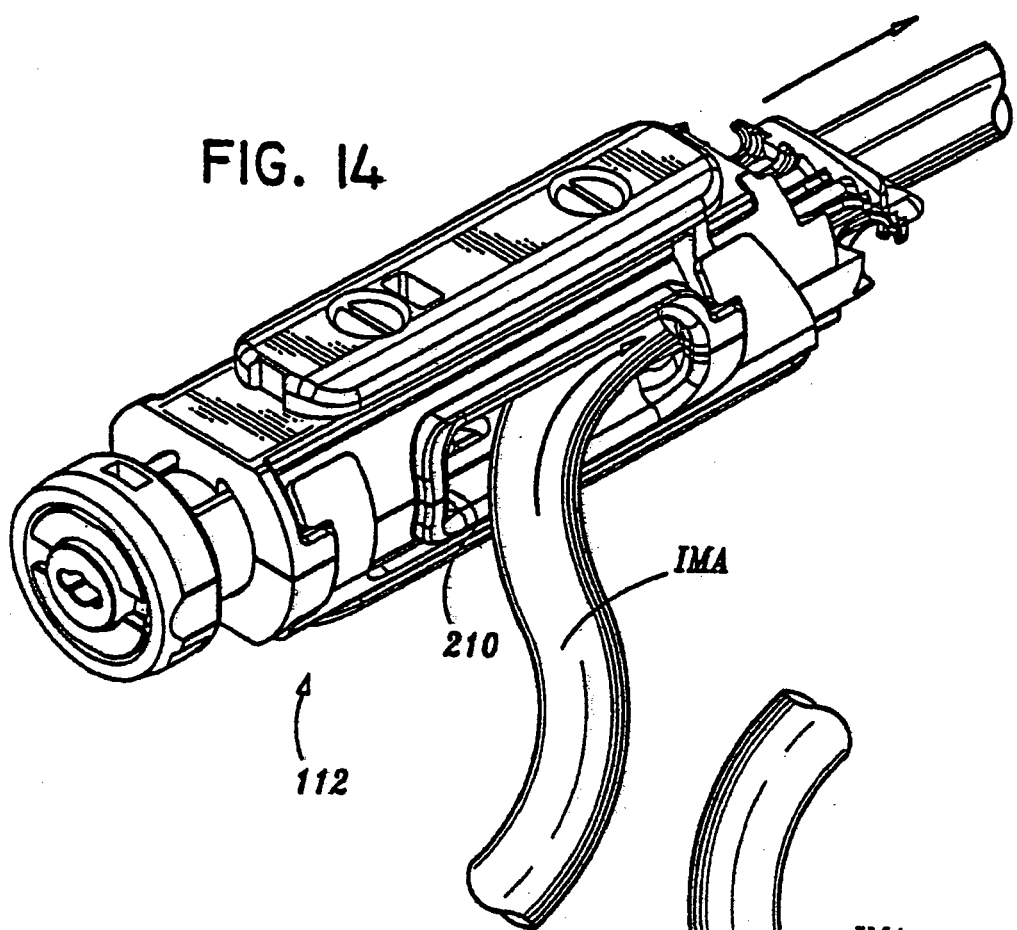
FIG. 14 is a perspective view of a disposable loading unit with a first vessel inserted therethrough.
Figure 15:
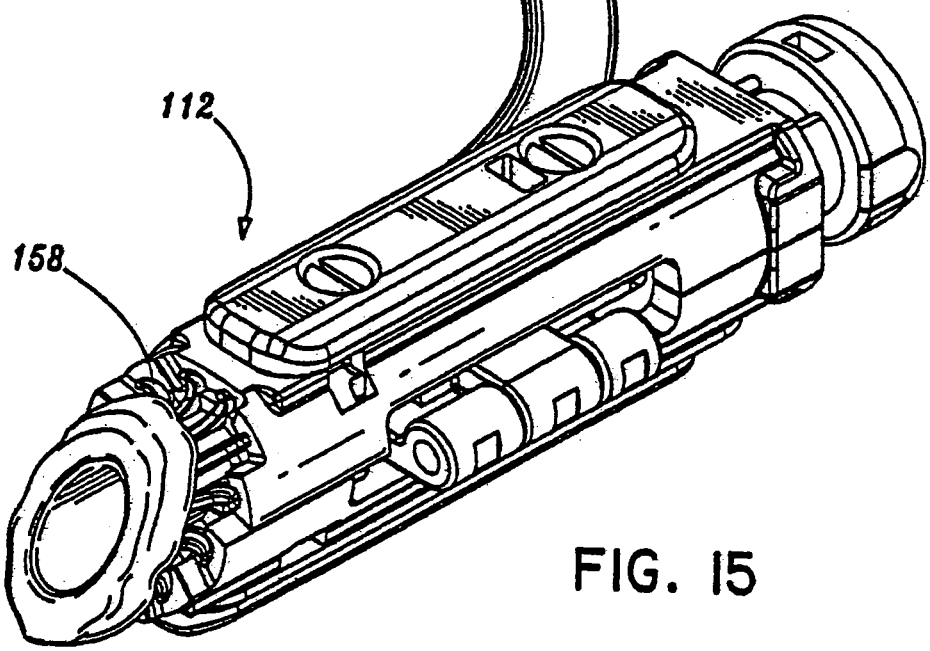
FIG. 15 is a perspective view of the disposable loading unit shown in reverse angle from that of FIG. 14, Which shows the vascular tissue everted over a plurality of surgical fasteners.
Figure 16:
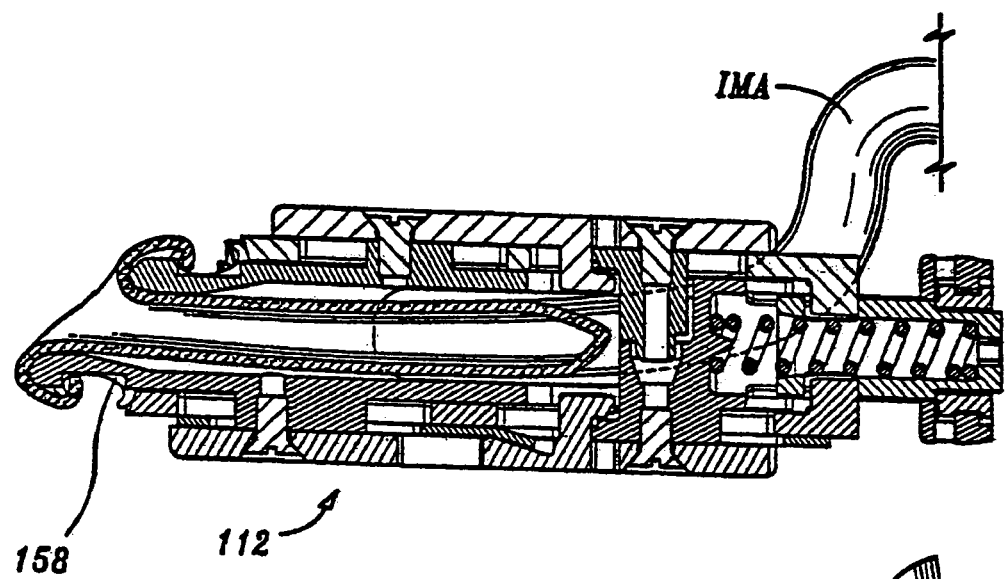
FIG. 16 is a horizontal cross-sectional view of the disposable loading unit of FIG. 15.
Figure 17:
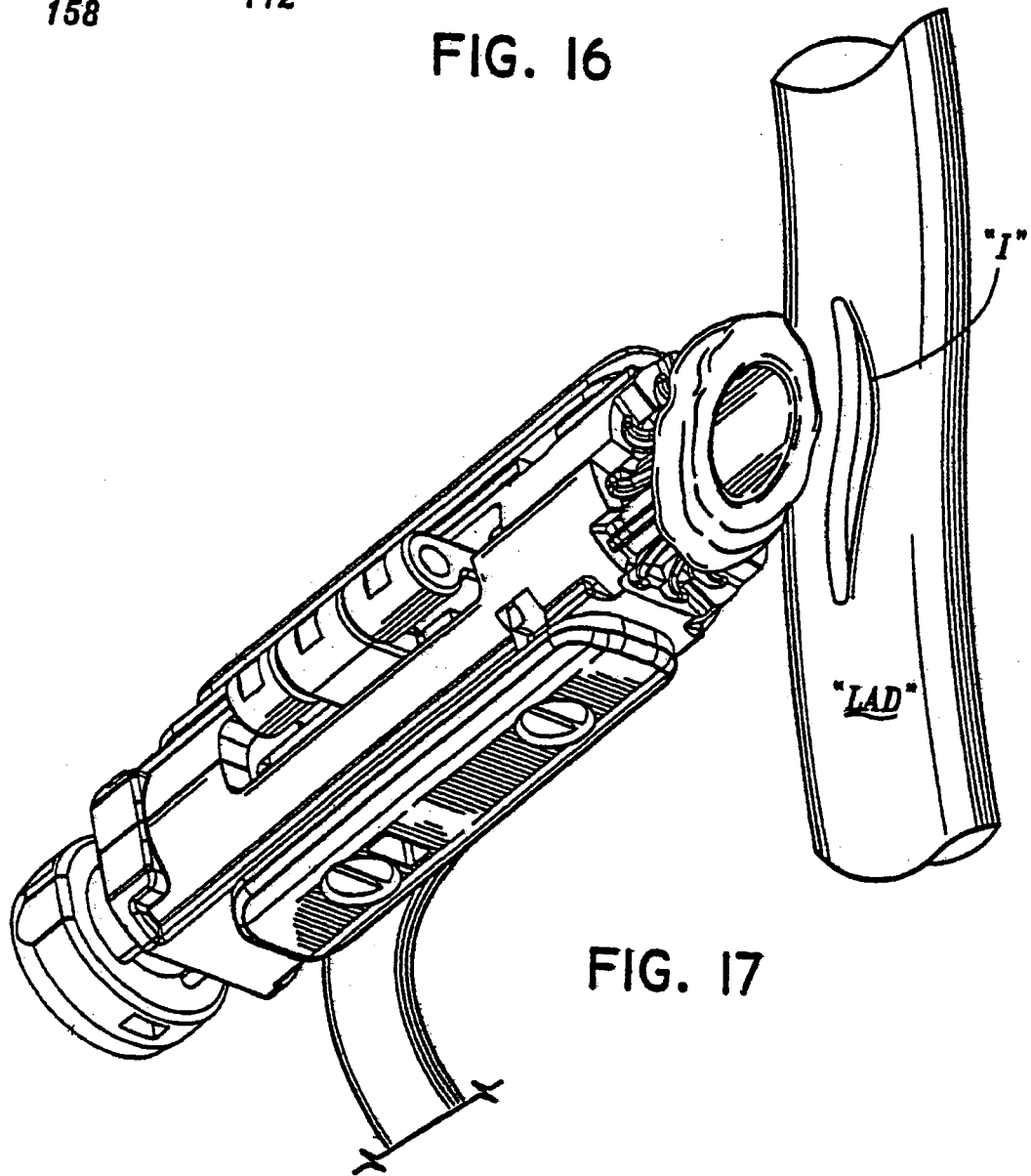
FIG. 17 is a perspective view showing insertion of the disposable loading unit and everted vascular tissue through a second vessel.
Figure 18:
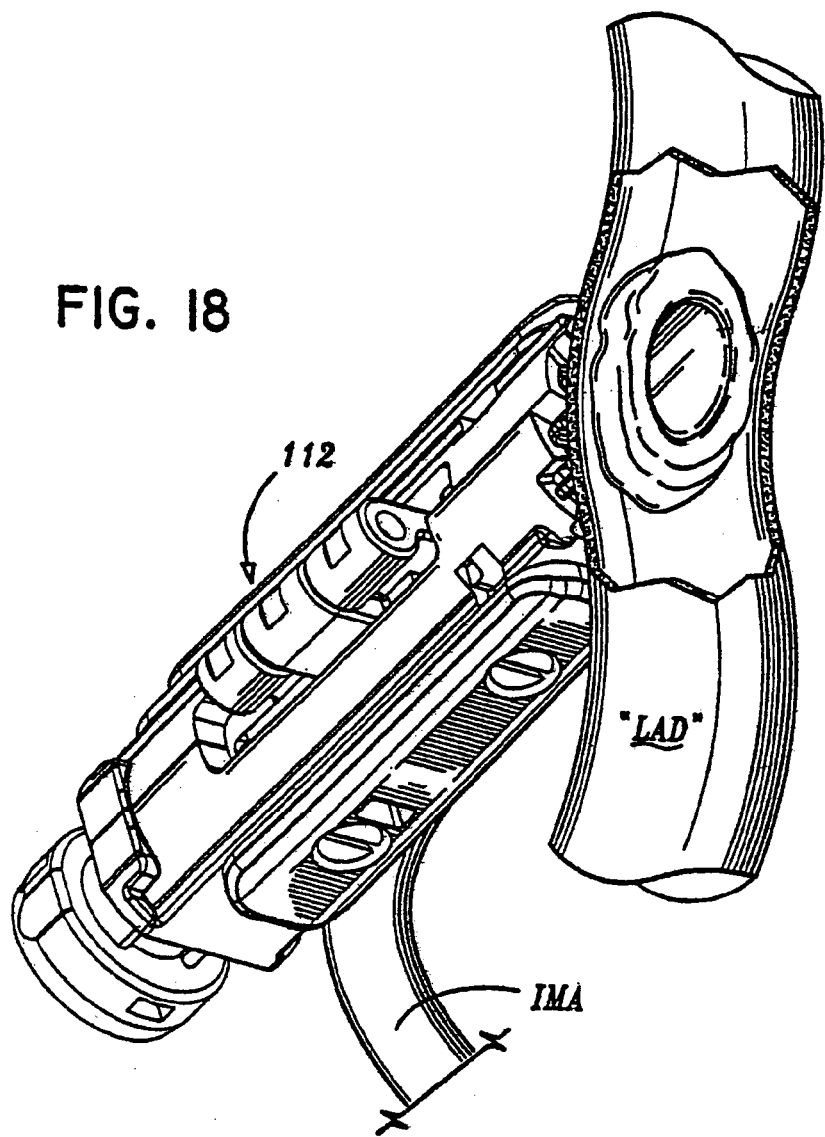
FIG. 18 is a view similar to FIG. 17, which shows full insertion of the distal end of the disposable loading unit with the everted vascular tissue through an incision formed in the second vessel.
Figure 19:
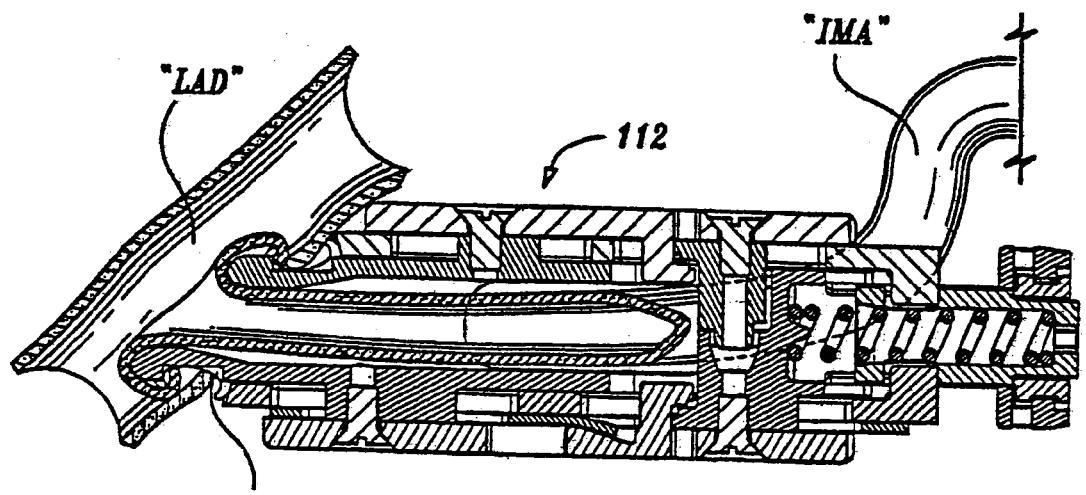
FIG. 19 is a horizontal cross-sectional view of the inserted disposable loading unit of FIG. 18.

Referring to FIG. 14, the free end of the IMA is inserted through lateral opening 210 of DLU 112 and passed out the distal end opening of the DLU. The free end of the IMA is then everted over the distal end of the DLU such that the end of the IMA is retained by the distal end oriented portions of clips 158 as best shown in FIG. 15 and FIG. 16. Everting of the tissue may be achieved by any suitable known techniques such as y using graspers. With the IMA loaded in DLU 112, the DLU is manipulated preferably detached from the handle and actuator assembly 110 in approximation to an incision "I" formed in the LAD, as shown in FIG. 17. Referring to FIGS. 18 and 19, the DLU with the everted IMA is inserted into the incision "I" of the LAD such that the walls of the LAD surrounding the incision are retained between the everted end of the IMA and the proximal ends of clips 158, as shown in FIG. 19.

As previously noted, the distal end of DLU 112 is configured with an angle relative to a transverse plane of the DLU in order to optimize the anastomosis and to facilitate optimal blood flow across the graft site from the IMA to the LAD. This junction creates "heel" and "toe" portions in which an acute or obtuse angle between the vessels is defined.

Once DLU 112 with the everted IMA has been successfully inserted through the incision of the LAD, the surgeon may then attach the handle/actuator assembly 110 to DLU 112 as shown in FIGS. 20 and 21. In particular, the DLU lock slide 217 is moved proximally as indicated by arrow "A" in order to retract-locking tube 215 and thereby expose the distal end of DLU holding tube 214, and in particular, semi-annular groove 230. DLU 112 is inserted on the distal end of the handle and actuator assembly 110 by placing mounting hub 138 within semi-annular groove 230 and releasing the force applied on DLU lock slide 217 as indicated by arrow "B" in FIG. 21, to permit coil spring 219 to return lock slide 217 and locking tube 215 to their distal-most orientations thereby securing the DLU in place.

Figure 25:
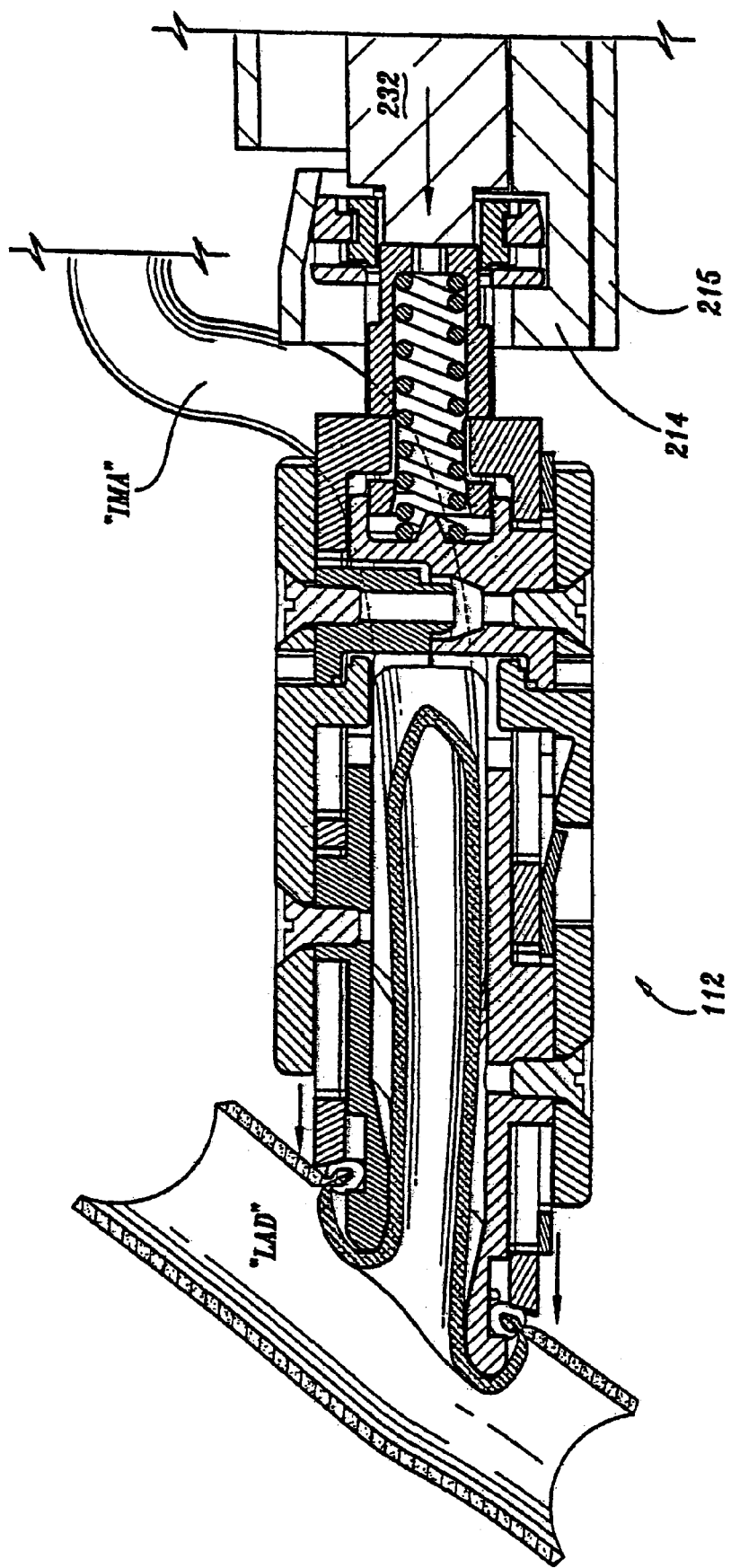
FIG. 25 is an enlarged horizontal cross-sectional view of the distal end of the handle/actuator assembly and the disposable loading unit, which shows the deformation of the surgical fasteners.
Figure 26:
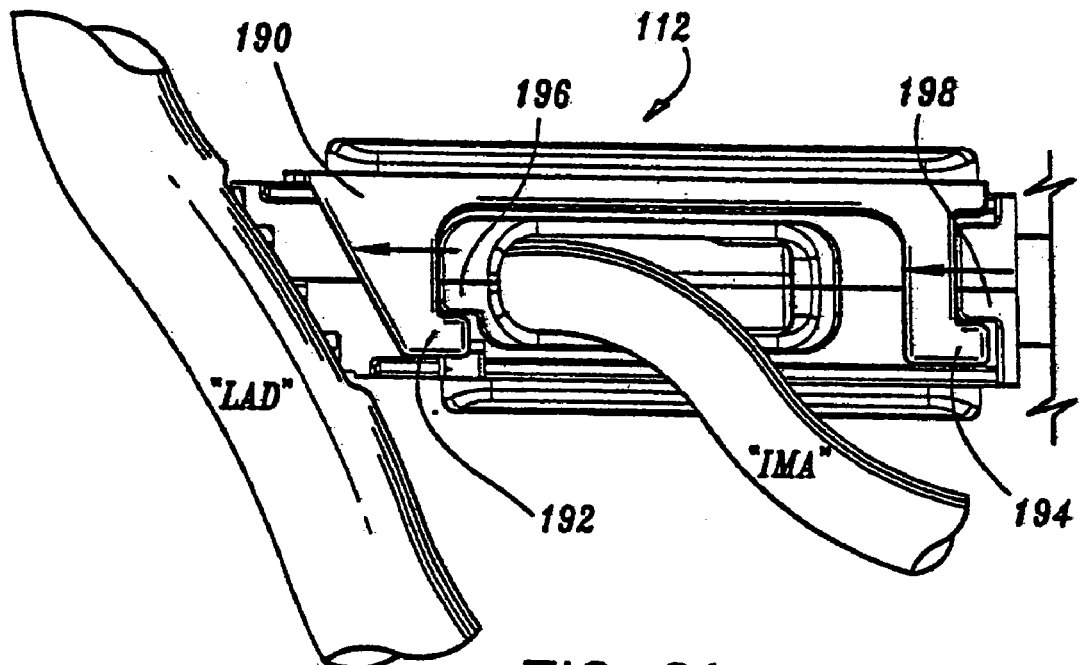
FIG. 26 is a side view showing operation of the disposable loading unit.
Figure 27:
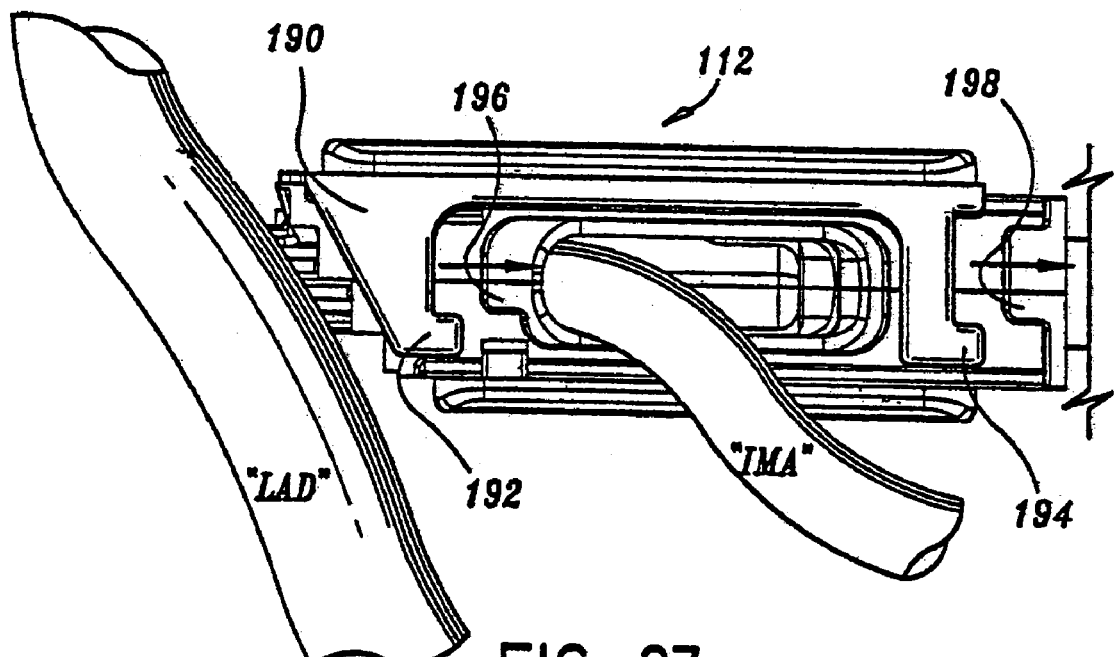
FIG. 27 is a view similar to FIG. 26, which shows retraction of a pusher member of the disposable loading unit after deformation of the surgical fasteners.

Referring to FIGS. 22 and 23, when the surgeon is ready to complete the anastomosis, the safety release slide 260 is moved proximally as indicated by arrow "C" in FIG. 23 thereby causing camming surface 268 to cam spring 250 downwardly away from shoulder 254 as indicated by arrow "D". Thereafter, the surgeon may depress cover 246 towards handle half-sections 212a and 212b, as indicated by arrow "E" in FIG. 24, causing actuator rod 232 to drive actuator 126 of DLU 112 distally as indicated by arrow "F", thereby moving pusher member split half-sections 160 and 160b distally to deform clips 158 as shown in FIGS. 25 and 26.

Figure 24:
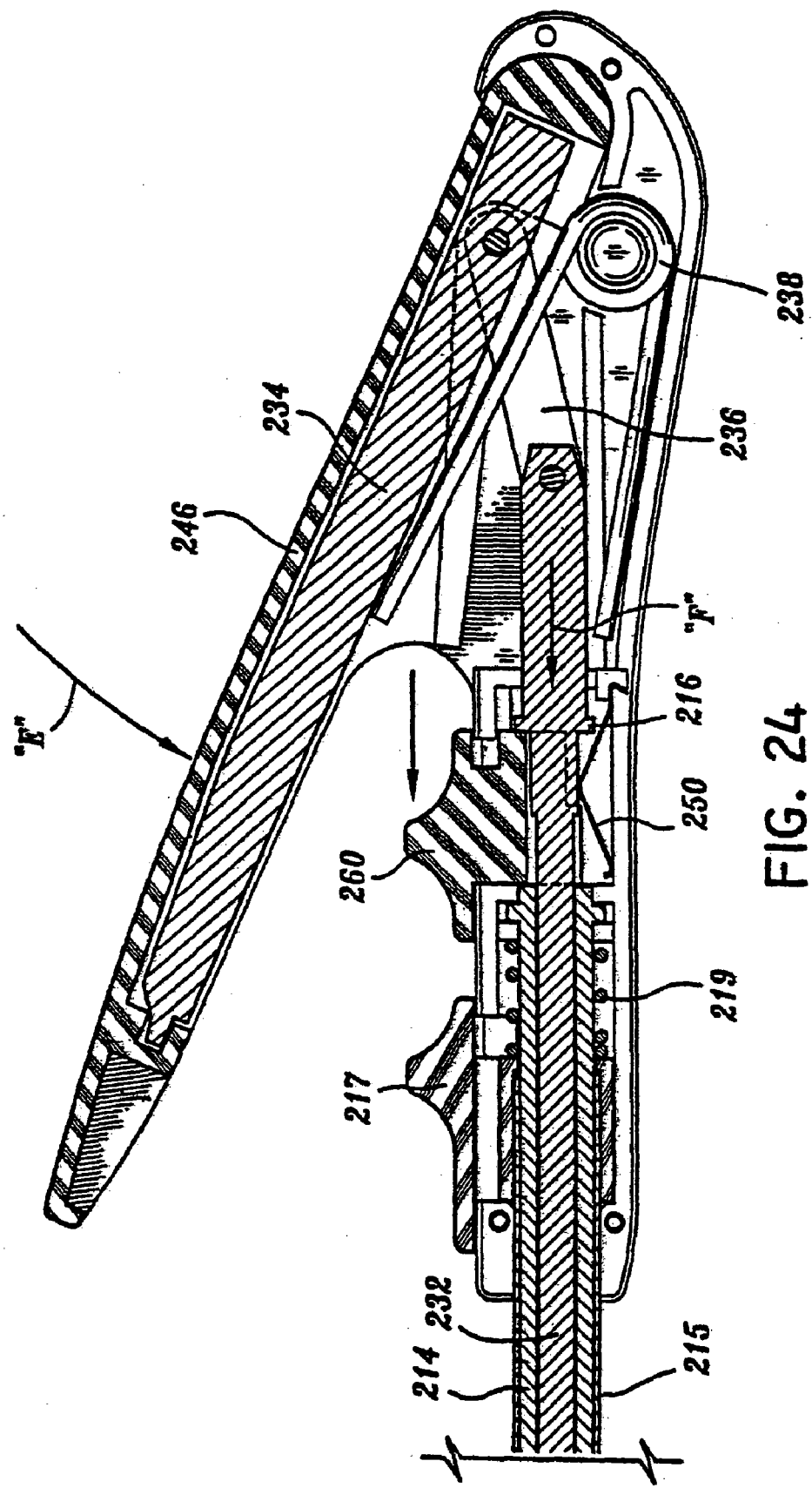
FIG. 24 is a horizontal cross-sectional view of the handle/actuator assembly, which shows the firing sequence of the handle/actuator assembly.

As best illustrated in FIG. 24, one particularly advantageous feature of the presently disclosed: surgical instrument is that upon actuation of handle/actuator assembly 110, safety release slide 260 is urged back into its initial locked orientation by way of annular flange 216 of actuator rod 232 pushing the lower portion of safety release slide 260 during the distal movement of actuator rod 232. In this manner, upon release of cover handle 246, the potential energy created by the compression of torsion spring 238 will cause actuator rod 232 to be pulled back proximally thereby engaging shoulder 254 with cutout 252 of spring 250. This will serve to prevent accidental re-firing action of surgical instrument 100.

Figure 31:
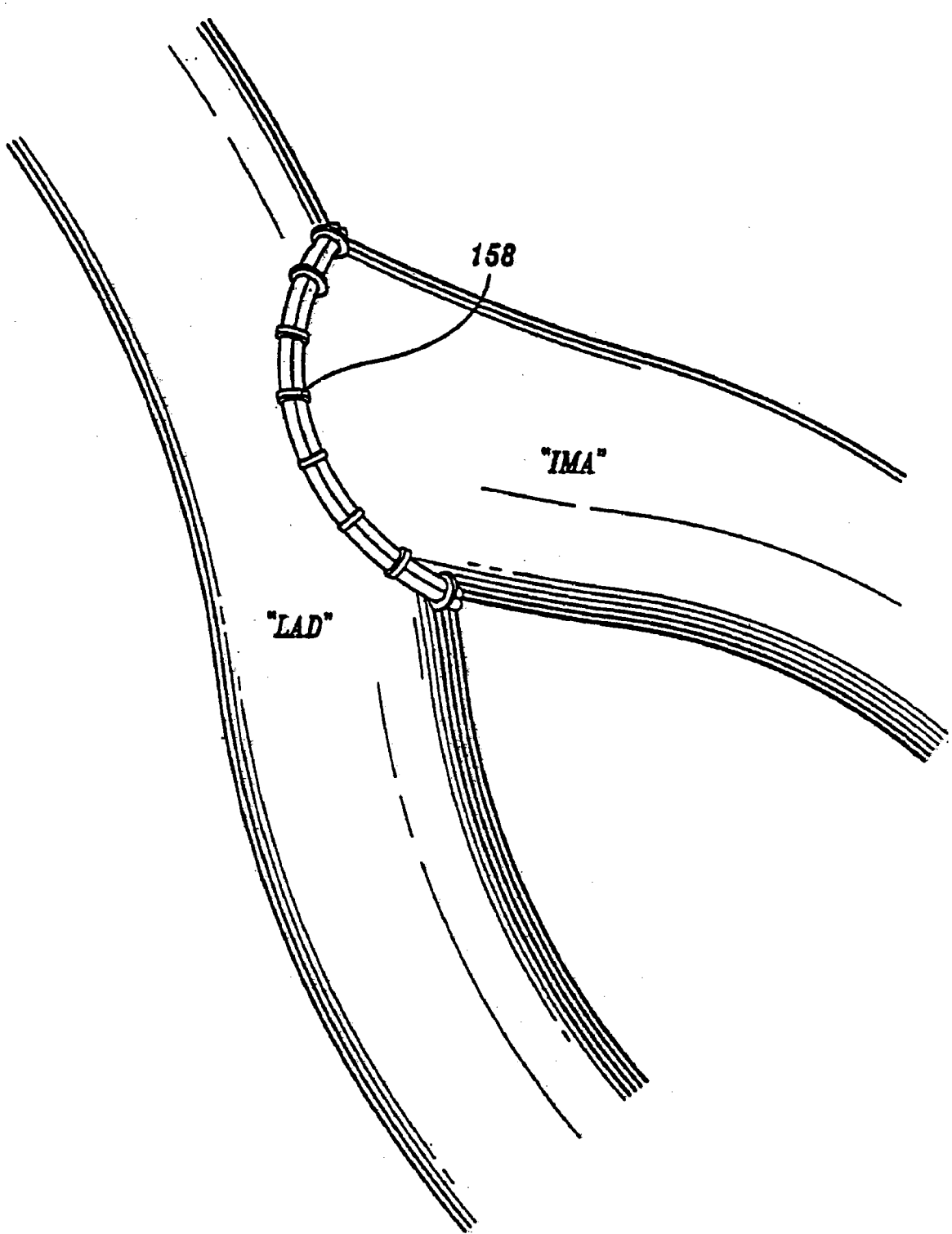
FIG. 31 is a view showing the completed anastomosis.

Referring to FIGS. 26–30, a further uniquely advantageous feature of surgical instrument 100 is hinge lock 190 and its operation. Upon firing of surgical instrument 100, return lockout tab 204 of hinge lock 190, which extended into lockout slot 208 during distal movement of hinge lock 190 with split half-sections 160 and 160b, serves to retain hinge lock 190 distal of its original seated location in tab receiving recess 206. By retaining hinge lock 190 at this position, latch portions 192 and 194 are released from raised surfaces 196 and 198 of split half-section 160a of the pusher member. In this manner, split half-section 116b and 160a may be pivoted away from split half-sections 116a and 160b as shown in FIG. 30 to permit the removal of the IMA from within the pathway of the DLU thereby completing the vascular anastomosis as shown in FIG. 31.

Figure 31A:
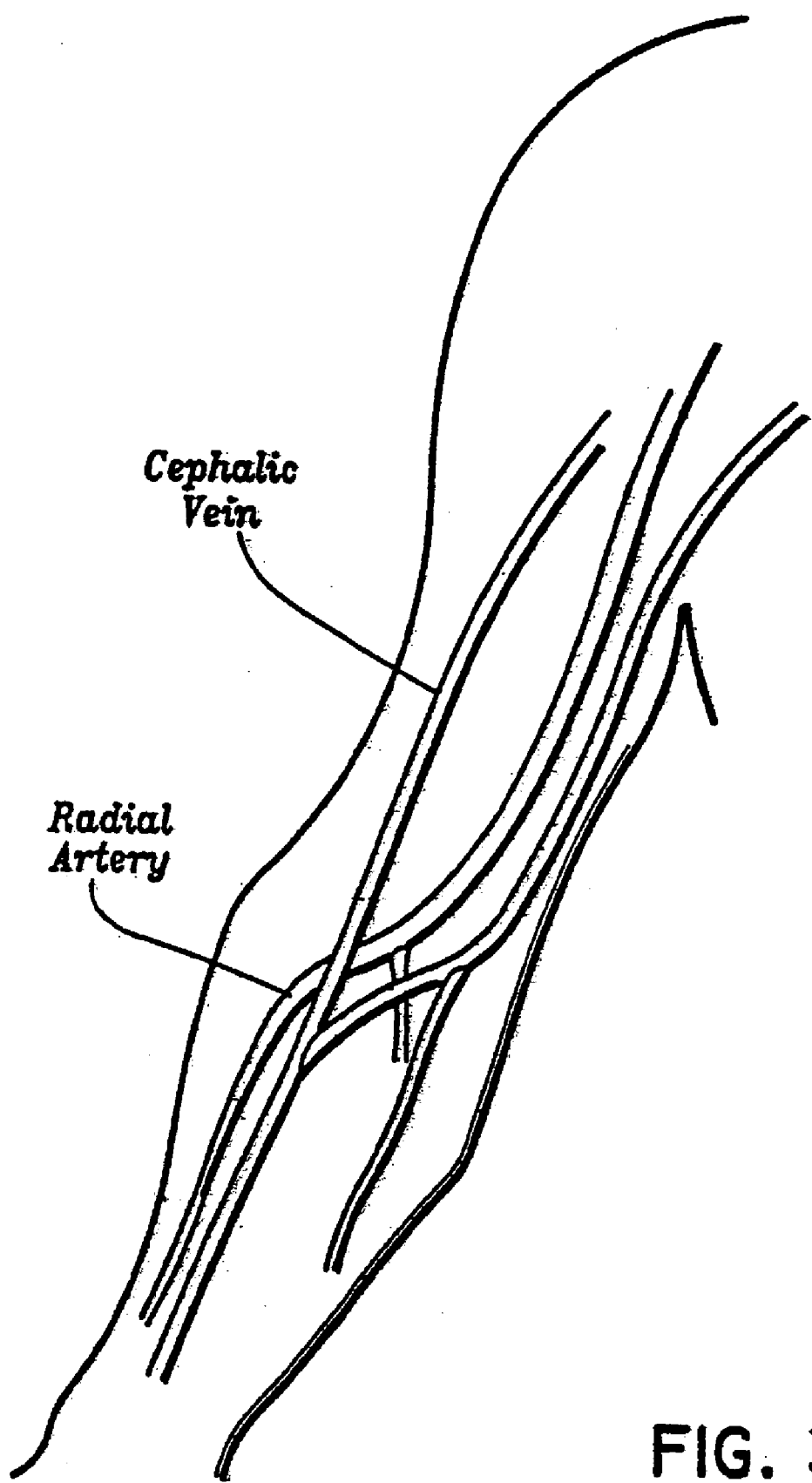
FIG. 31A is a view showing an alternative anastomosis site for a procedure known as an A-V fistula.
Figure 32:
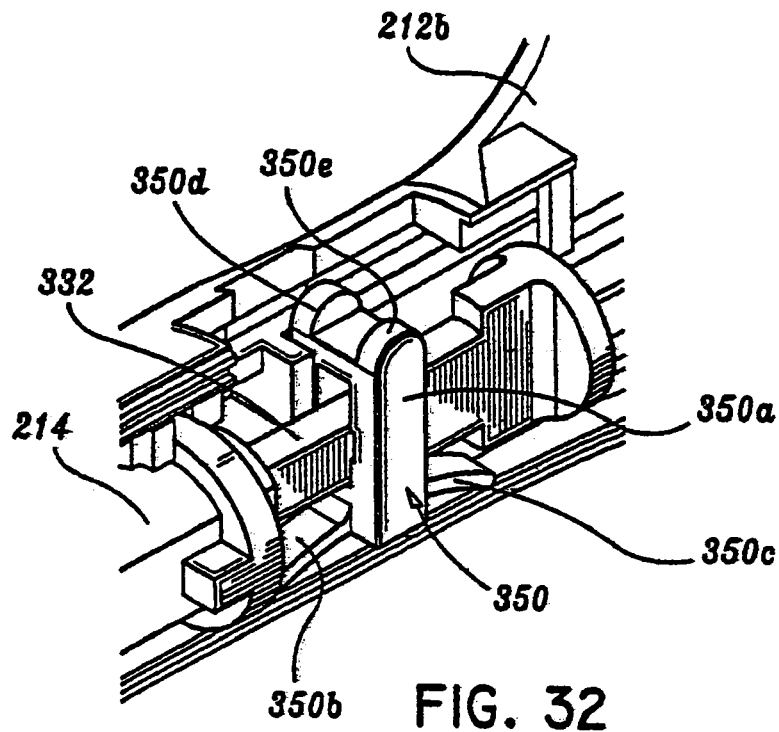
FIG. 32 is a perspective view of an alternative embodiment of a safety firing lockout member of the handle/actuator assembly.

Referring to FIG. 31A, a portion of the vascular anatomy of an arm which may be an alternative utilized anastomosis site as illustrated wherein instead of joining the IMA to the LAD in a bypass procedure, an A-V fistula is performed utilizing surgical instrument 100 to join the radial artery end-to-side with the cephalic vein (sometimes called the radial vein). Other A-V fistulas which may also be achieved utilizing surgical instrument 100 include joining the ulnar artery end-to-side with the basilic vein (sometimes called the ulnar vein). Such A-V fistulas are performed to facilitate hemodialysis for end stage kidney disease to allow a single puncture at the dialysis unit for blood cleansing. The fistula allows a greater flow Tate through the dialyzer (not shown).

Figure 33:
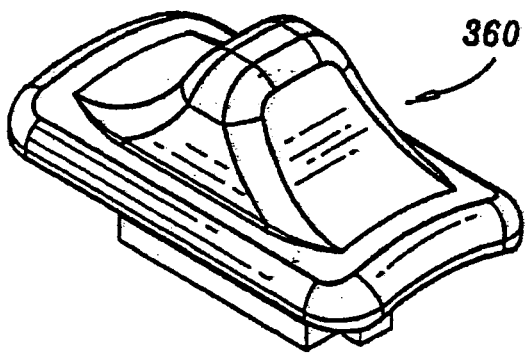
FIG. 33 is a perspective view of a safety release slide of the embodiment of FIG. 32, FIG. 33A, is a perspective view showing the bottom of the safety release slide of FIG. 33.
Figure 33A:
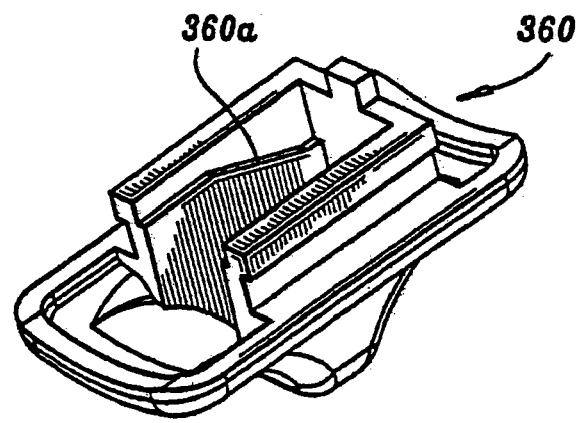
Figure 34:
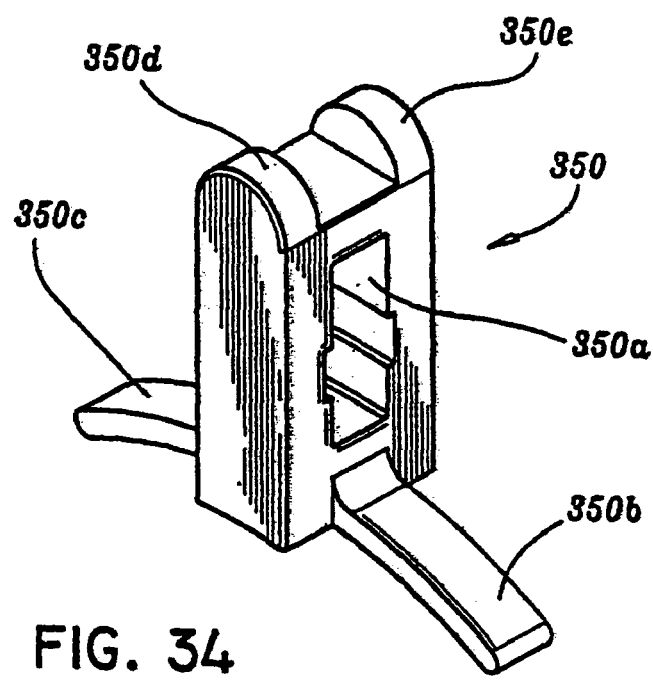
FIG. 34 is a perspective view of a lockout spring of the safety firing lockout of FIG. 32.
Figure 35:
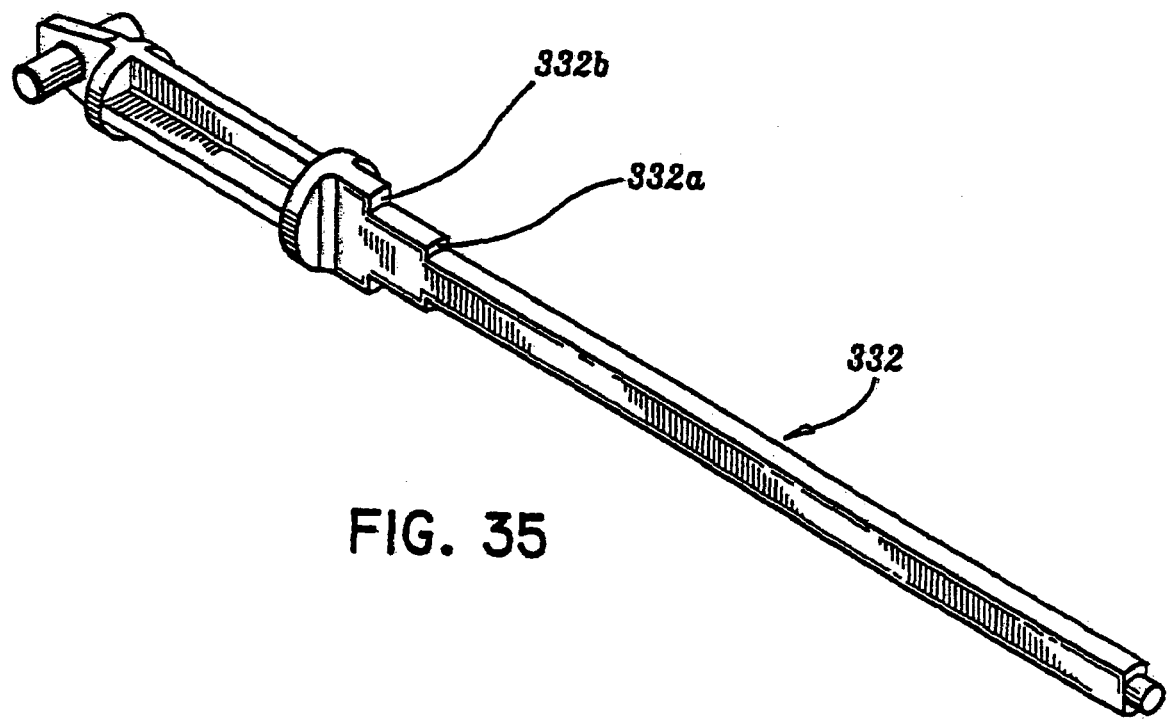
FIG. 35 is a perspective view of an actuator rod of the embodiment of FIG. 32.

Referring to FIGS. 32–39, an alternative embodiment of the firing safety mechanism illustrated in FIGS. 22–24 is illustrated which also prevents the unintended firing of surgical instrument 100. The firing safety mechanism includes a lock spring 350 and a safety release slide 360. Referring to FIGS. 33 and 33A, safety release slide 360 includes a pair of camming surfaces 360a and 360b which interact with cam follower surfaces 350d and 350e. Lock spring 350, as best illustrated in FIG. 34, includes a body portion 350a that defines a yoke, a pair a leaf spring portions 350b and 350c, and a pair of cam follower surfaces 350d and 350e formed along a top portion thereof. An actuator rod 332, FIG. 35, is configured and dimensioned to pass through yoke portion 350a of lock spring 350.

Figure 36:
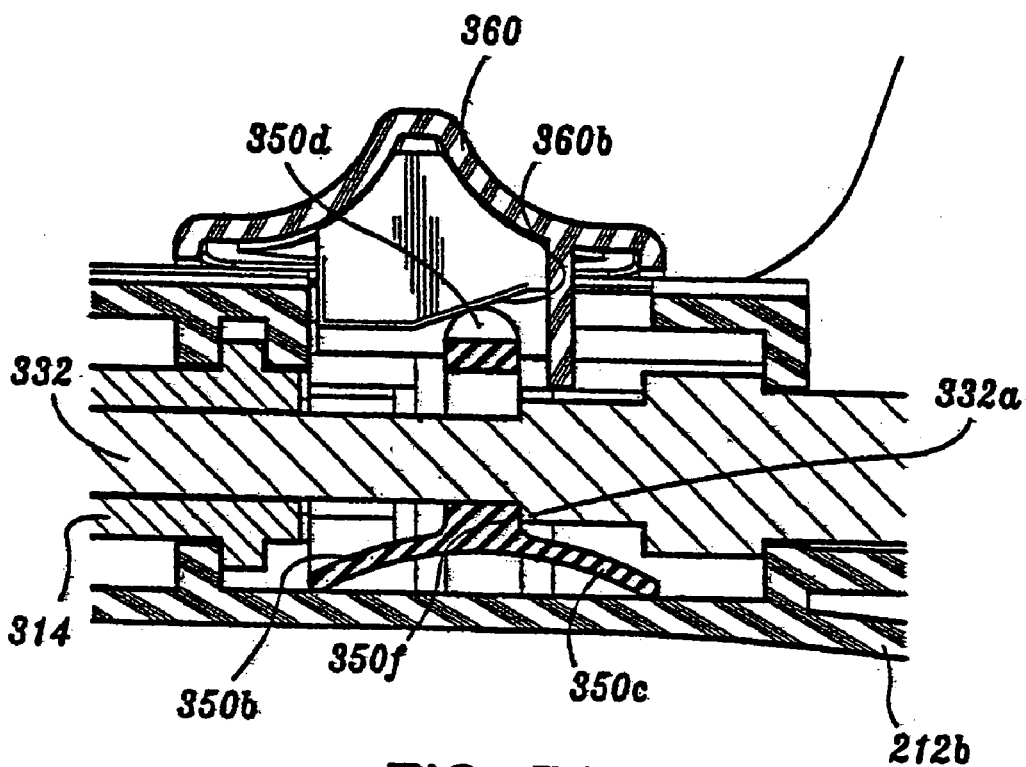
FIG. 36 is a partial cross-sectional view illustrating the initial lockout configuration of the safety firing lock-out mechanism of FIG. 32.

In the initial (pre-fired) configuration, as shown in FIG. 36, safety release slide 360 is disposed above lock spring 350 such that camming surfaces 360a and 360b contact cam following surfaces 350e and 350e, respectively, when safety release slide 360 is in the distal-most position. In this orientation, leaf spring portions 350b and 350c serve to bias lock spring 350 upwardly within the instrument housing so that a shoulder portion 332a of actuator rod 332 abuts against a proximal facing lower surface 350f, as shown in FIG. 36, to prevent firing of the instrument.

Figure 37:
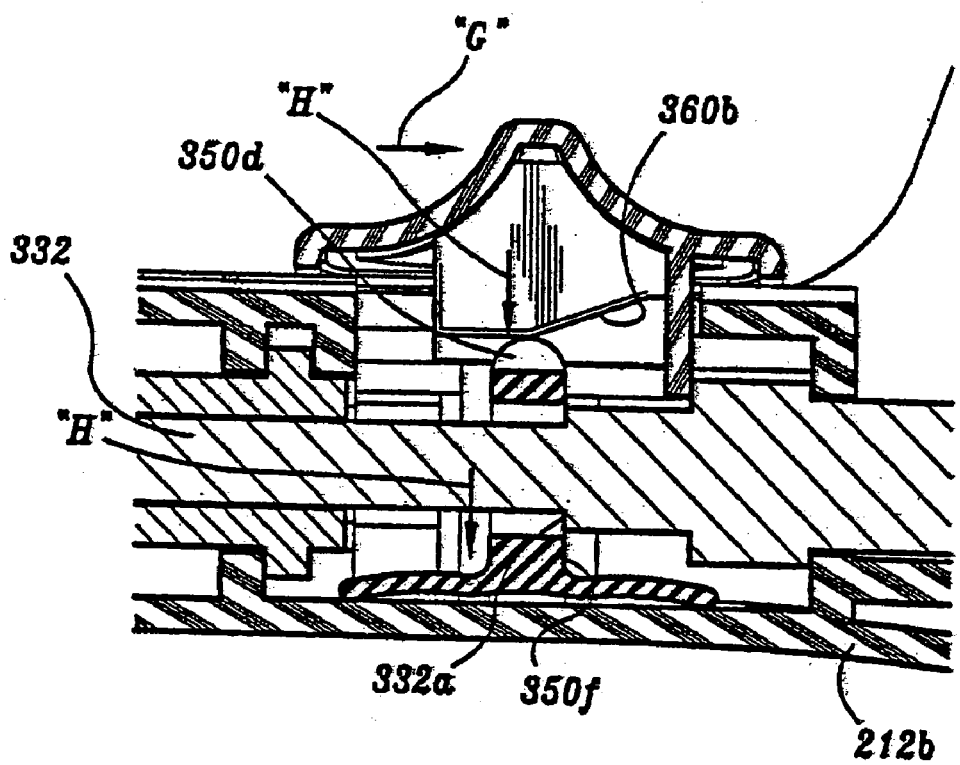
FIG. 37 is a view similar to FIG. 36, which illustrates an operational sequence of the safety firing lockout mechanism.

When the surgeon desires to fire the instrument, safety release slide 360 is moved proximally as indicated by arrow "G" in FIG. 37. In this manner, camming surfaces 360a and 360b travel over cam follower surfaces 350e and 350d, respectively, thereby urging lock spring 350 downwardly in the direction of arrows "H" to overcome the spring force of leaf spring portions 350b and 350c. This movement displaces proximal surface 350f below shoulder portion 332a thereby permitting actuator rod 332 to move distally.

Figure 38:
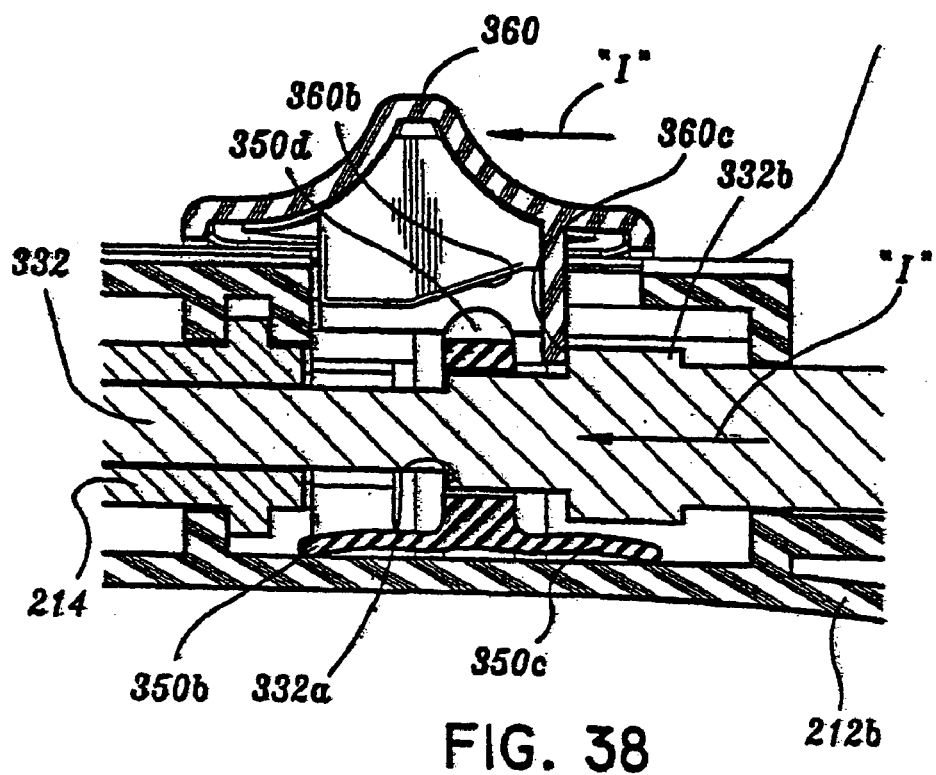
FIG. 38 is a view similar to FIG. 36 which illustrates an operational sequence of the safety firing lockout mechanism.
Figure 39:
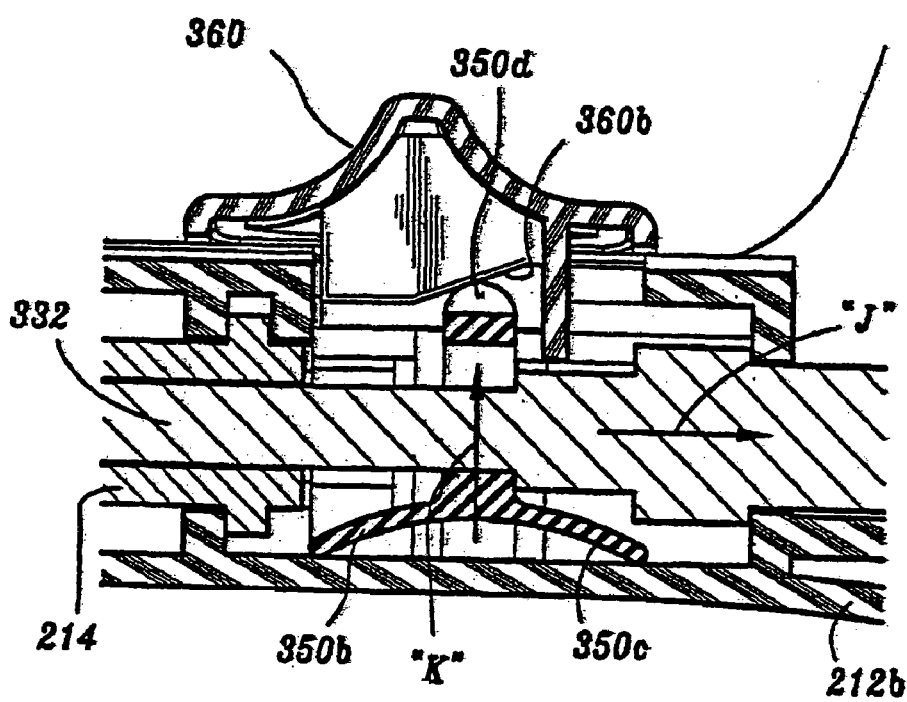
FIG. 39 is a view similar to FIG. 36 which illustrates a further operational sequential view of the safety firing lockout mechanism.

Upon distal movement of actuator rod 332 as indicated by arrow "I" in FIG. 38, a second shoulder portion 332b formed proximal of shoulder portion 332a on actuator rod 332 contacts a rear wall portion 360c of safety release slide 360 thereby urging safety release slide distally in a direction of arrow "I" as well. Upon release of actuator handle cover 246, actuator rod 332 moves proximally as indicated by arrow "J" in FIG. 39 thereby permitting lock spring 350 to move upwardly as indicated by arrow "K" in FIG. 39 to reset the firing safety mechanism.

It will be understood that various modifications may be made to the embodiment shown herein. For example, the instruments may be sized to perform an anastomosis for other vessels and luminal tissue. Therefore, the above description should not be construed as limiting, but merely as exemplifications of preferred embodiments. Those skilled in the art will envision other modifications within the scope and spirit of the claims appended hereto.

What is claimed is:

1. A surgical instrument for performing an anastomosis, comprising:
   a housing;
   an actuator attached to the housing, said actuator including an actuating rod being selectively movable to deform at least one surgical fastener;
   a firing safety mechanism including a leaf spring having at least one cut out defined therethrough which engages said housing, said cut out of said leaf spring configured to engage a shoulder portion of said actuator to prevent distal movement of said actuator when disposed in an armed position; and
   a safety release being selectively activateable to disarm said leaf spring to allow activation of said actuator.

2. A surgical instrument according to claim 1 wherein said safety release includes a camming surface which, upon movement thereof, cams said cut out of said leaf spring out of engagement with said actuator.

3. A surgical instrument according to claim 1 wherein said leaf spring includes a hook-like member which secures said leaf spring to said housing.

4. A surgical instrument according to claim 1 wherein said safety release includes an upwardly extending contact surface which facilitates actuation of said safety release.

* * * * *